United States Patent
Hogan et al.

(10) Patent No.: US 10,954,483 B2
(45) Date of Patent: Mar. 23, 2021

(54) SYSTEM, METHOD, AND DEVICE FOR HIGH-THROUGHPUT, AUTOMATED CULTURING OF GENETICALLY MODIFIED ORGANISMS

(71) Applicant: The Trustees of the University of Pennsylvania, Philadelphia, PA (US)

(72) Inventors: Michael Hogan, Schwenksville, PA (US); Orkan M. Telhan, Philadelphia, PA (US); Karen Hogan, Philadelphia, PA (US)

(73) Assignee: THE TRUSTEES OF THE UNIVERSITY OF PENNSYLVANIA, Philadelphia, PA (US)

( * ) Notice: Subject to any disclaimer, the term of this patent is extended or adjusted under 35 U.S.C. 154(b) by 280 days.

(21) Appl. No.: 15/557,706

(22) PCT Filed: Mar. 11, 2016

(86) PCT No.: PCT/US2016/021953
§ 371 (c)(1),
(2) Date: Sep. 12, 2017

(87) PCT Pub. No.: WO2016/145290
PCT Pub. Date: Sep. 15, 2016

(65) Prior Publication Data
US 2018/0051243 A1 Feb. 22, 2018

Related U.S. Application Data

(60) Provisional application No. 62/131,910, filed on Mar. 12, 2015.

(51) Int. Cl.
*C12M 1/00* (2006.01)
*B01L 3/00* (2006.01)
(Continued)

(52) U.S. Cl.
CPC .......... *C12M 33/04* (2013.01); *B01J 19/0046* (2013.01); *C12M 23/44* (2013.01);
(Continued)

(58) Field of Classification Search
None
See application file for complete search history.

(56) References Cited

U.S. PATENT DOCUMENTS

| 4,681,741 A | 7/1987 | Hanaway | |
|---|---|---|---|
| 4,719,087 A * | 1/1988 | Hanaway | B01L 3/5085 422/551 |

(Continued)

FOREIGN PATENT DOCUMENTS

| EP | 0355266 | 2/1990 |
|---|---|---|
| WO | 2015/017858 | 2/2015 |

OTHER PUBLICATIONS

International Patent Application No. PCT/US2016/021953, Notification of Transmittal of the International Search Report and the Written Opinion of the International Searching Authority dated May 23, 2016, 13 pages.

(Continued)

*Primary Examiner* — Nathan A Bowers
(74) *Attorney, Agent, or Firm* — Morgan, Lewis & Bockius LLP

(57) ABSTRACT

A fluid transfer system includes a transfer carousel capable of rotational and/or translational movement; at least one holding vessel (e.g. syringe) having a plunger, wherein the syringe is connected to the transfer carousel such that the movement of the transfer carousel results in movement of the syringe and wherein the syringe is capable of translational movement relative to the transfer carousel; a drive motor connected to the syringe that is capable of controlling the position of the plunger; and a peripheral module com- (Continued)

prising at least one vessel that is capable of containing a fluid, wherein the vessel has an opening that can be mated with the syringe to allow fluid transfer between the vessel and the syringe. Methods for transferring a fluid are also disclosed.

17 Claims, 9 Drawing Sheets

(51) Int. Cl.
    *C12M 1/26*     (2006.01)
    *C12M 3/00*     (2006.01)
    *C12M 1/42*     (2006.01)
    *B01J 19/00*     (2006.01)
    *C12M 1/34*     (2006.01)
    *C12M 1/36*     (2006.01)

(52) U.S. Cl.
CPC ............ *C12M 23/50* (2013.01); *C12M 31/04* (2013.01); *C12M 35/02* (2013.01); *C12M 41/34* (2013.01); *C12M 41/46* (2013.01); *C12M 41/48* (2013.01); *C12M 47/06* (2013.01); *C12M 47/12* (2013.01); *B01J 2219/0029* (2013.01); *B01J 2219/0054* (2013.01); *B01J 2219/0074* (2013.01); *B01J 2219/00326* (2013.01); *B01J 2219/00353* (2013.01); *B01J 2219/00376* (2013.01); *B01J 2219/00547* (2013.01); *B01J 2219/00576* (2013.01); *B01J 2219/00691* (2013.01); *B01J 2219/00702* (2013.01)

(56) References Cited

U.S. PATENT DOCUMENTS

| | | | |
|---|---|---|---|
| 5,046,496 | A | 9/1991 | Betts et al. |
| 5,620,898 | A | 4/1997 | Yaremko et al. |
| 8,507,263 | B2 | 9/2013 | Asnaghi et al. |
| 2002/0090320 | A1* | 7/2002 | Burow ............... B01L 9/523 422/64 |
| 2004/0156823 | A1 | 8/2004 | Reinecke et al. |
| 2005/0255006 | A1* | 11/2005 | Romaguera ......... B01L 3/0227 422/525 |
| 2006/0093530 | A1* | 5/2006 | Ueda ............... B01L 9/543 422/400 |
| 2007/0105214 | A1 | 5/2007 | Micklash, II et al. |
| 2007/0142777 | A1 | 6/2007 | Klein |
| 2009/0024009 | A1 | 1/2009 | Freeman et al. |
| 2009/0042281 | A1 | 2/2009 | Chang et al. |
| 2009/0088336 | A1* | 4/2009 | Burd .................. B01J 19/0046 506/9 |
| 2012/0073389 | A1* | 3/2012 | Herve .................. G01N 9/00 73/864.21 |
| 2012/0325365 | A1 | 12/2012 | Strangis |
| 2013/0130369 | A1* | 5/2013 | Wilson ................ G16B 99/00 435/289.1 |
| 2013/0150266 | A1 | 6/2013 | Klein |
| 2013/0210130 | A1 | 9/2013 | Larcher et al. |
| 2014/0170735 | A1* | 6/2014 | Holmes ................ G01N 21/07 435/287.1 |
| 2014/0302597 | A1 | 10/2014 | Zhou et al. |
| 2016/0186166 | A1* | 6/2016 | Poehmerer ........ B01L 3/502761 205/420 |
| 2017/0052165 | A1 | 2/2017 | Zapata Penasco et al. |
| 2017/0198246 | A1 | 7/2017 | Niazi |
| 2018/0147118 | A1* | 5/2018 | Garfield ............... A61J 1/2089 |

OTHER PUBLICATIONS

Supplementary European Search Report EP16762580.5 dated Sep. 3, 2018, 8 pages.

Markov, D., "Thick-tissue bioreactor as a platform for long-termin organotypic culture and drug delivery" NIH Public Access Author Manuscript; published as Lab Chip. Nov. 7, 2002; 12(21): doi:10.1039/c2lc40304h; 17 pages.

Perez-Pinera, P. "Synthetic biology and microbioreactor platforms for programmable production of biologics at the point-of-care"; Nature Communications; published Jul. 29, 2016 DOI:10.1038/ncomms12211; 10 pages.

Tandon, N. "Portable bioreactor for perfusion and electrical stimulation of engineered cardiac tissue"; HHS Public Access, Author Manuscript; Published in final edited form as: Conf Proc IEEE Eng Med Biot Soc. 2013 ; 2013: 6219-6223. doi:10.1109/EMBC.2013.6610974.

K. Muffler "Application of Biofilm Bioreactors in White Biotechnology"; Adv Biochem Eng Biotechnol (2014) 146: 123-161 DOI: 10.1007/10_2013_267; Springer-Verlag Berlin Heidelberg 2014 Published Online: Jan. 9, 2014 39 pages.

European Official Action of Application 16 762 580.5 dated Sep. 18, 2019 (4 pages).

* cited by examiner

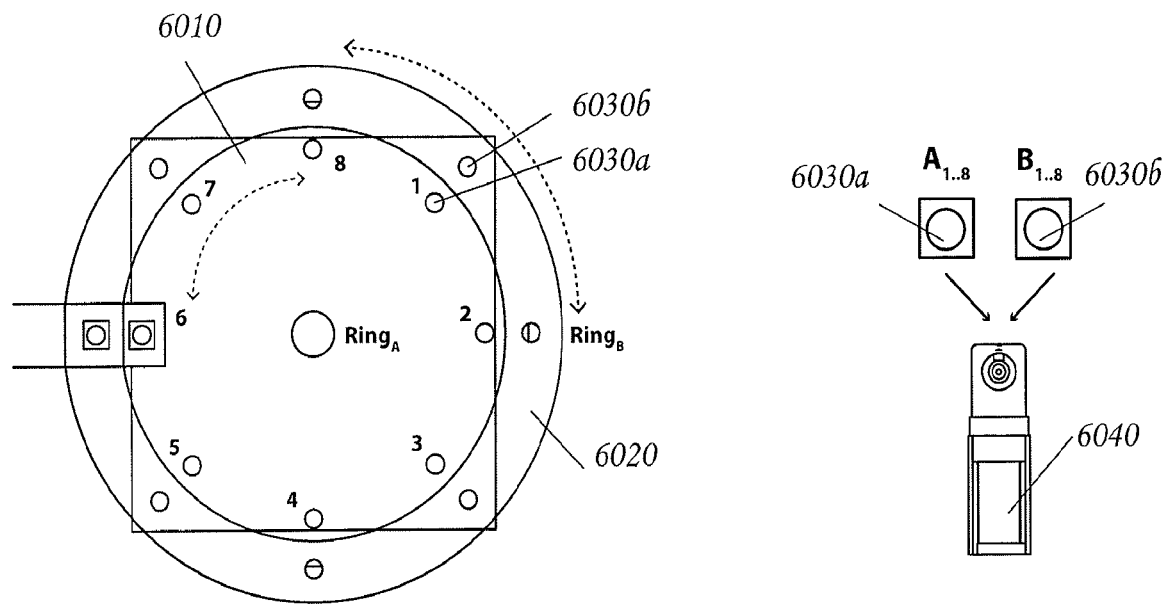
Combinatorial mixing of inputs
stored at rings A and B
Fig. 6A
Fig. 6B
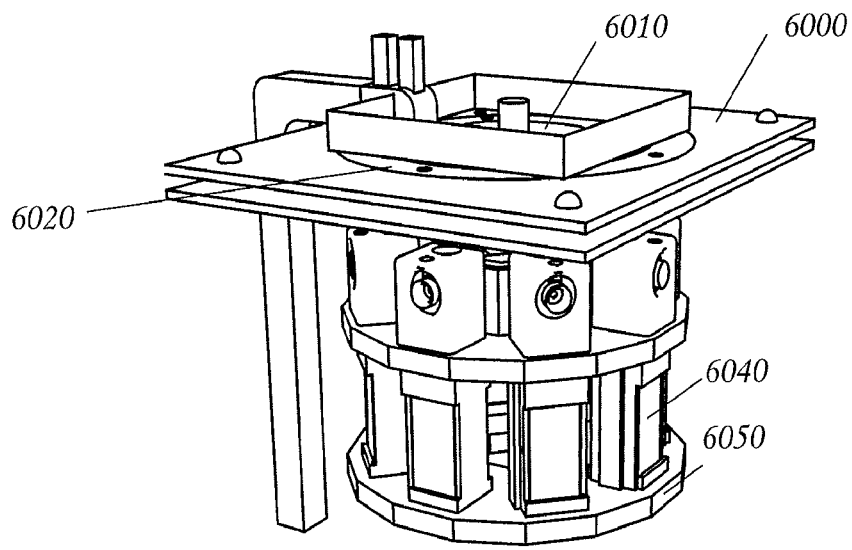
Multiplexing inputs
into individual vessels
Fig. 6C

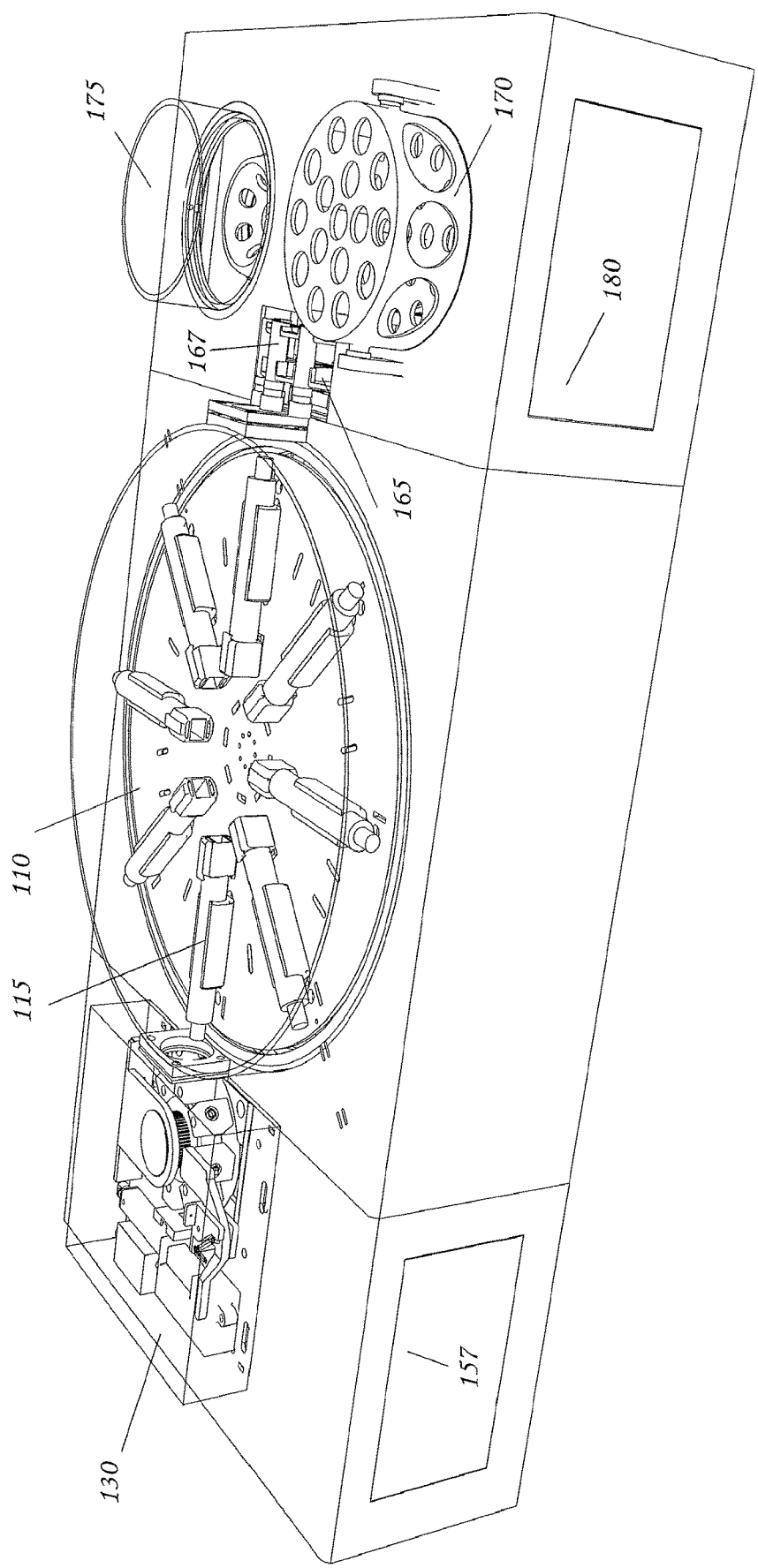

SYSTEM, METHOD, AND DEVICE FOR HIGH-THROUGHPUT, AUTOMATED CULTURING OF GENETICALLY MODIFIED ORGANISMS

CROSS REFERENCE TO RELATED APPLICATIONS

This application is a U.S. National Stage filing of International Patent Application No. PCT/US2016/021953, filed Mar. 11, 2016, which claims the benefit of U.S. Provisional Application Ser. No. 62/131,910, filed Mar. 12, 2015, the entire disclosure of each is incorporated herein by reference in its entirety for all purposes.

This application claims the benefit of U.S. Provisional Application Ser. No. 62/131,910, filed Mar. 12, 2015, which is incorporated herein by reference in its entirety.

FIELD OF THE INVENTION

The present invention generally relates to a material transfer and/or culture system and, more particularly, to a system and method for highly automated handling of most aspects of preparation of cells for culture, including modular elements for transformation and/or transfection, control of the culture itself, harvesting, etc. The invention describes devices and corresponding methods that, together, comprise a platform and system that automates most aspects of cell culture, and does so in a manner that permits high throughput at low cost by virtue of parallelism and in situ analytics and control. As a consequence of the system's overall design, it also affords superior curation of data regarding the dynamics of the culture process.

BRIEF SUMMARY OF THE INVENTION

In some embodiments a material transfer and/or culture system comprises a transfer carousel capable of rotational and/or translational movement; at least one syringe having a plunger, wherein the syringe is connected to the transfer carousel such that the movement of the transfer carousel results in movement of the syringe and wherein the syringe is capable of translational movement relative to the transfer carousel; a drive motor connected to the syringe that is capable of controlling the position of the plunger; and a peripheral module comprising at least one vessel that is capable of containing a fluid, wherein the vessel has an opening that can be mated with the syringe to allow fluid transfer between the vessel and the syringe. In some embodiments the plunger is threaded. In some embodiments the fluid transfer system is a closed system. As used herein embodiments of the system are commonly referred to as a material transfer system, a fluid transfer system, or a cell culture system; however it is understood that in some embodiments the number of vessels used are minimized and/or the number of fluid and/or material transfers are minimized.

In some embodiments a fluid transfer system includes a syringe that includes a plunger drive mechanism that passes through the plunger. In some embodiments the drive motor is housed partially or fully within the body of the syringe. In some embodiments a fluid transfer system includes a syringe that further includes analysis instrumentation, wherein the analysis instrumentation is embedded in the plunger, in a plug with the syringe, or within a structure surrounding the syringe, and is capable of monitoring the contents of the syringe. In some embodiments a fluid transfer system includes a syringe, wherein the plunger of the syringe comprises one or more bores that pass through the plunger, and permit monitoring of gas tension in the contents of the syringe and/or control of gas tension in the contents of the syringe. In some embodiments the fluid transfer system includes a syringe that comprises a rolling diaphragm. In some embodiments the rolling diaphragm vessel is a disposable item. In some embodiments the syringe comprises a drive motor and a plunger drive mechanism, which may pass through the plunger. In some embodiments the drive motor is housed partially or fully within the body of the syringe. In some embodiments the syringe comprises a commercially available, disposable syringe. In some embodiments the syringe includes miniaturized analytical instrumentation embedded in the plunger that is capable of monitoring contents of the syringe.

In some embodiments the syringe further comprises one or more ports that pass through the plunger and permit monitoring of gas tension in contents of the syringe and/or control of gas tension in the contents of the syringe In some embodiments a syringe, or a peripheral module, or both the syringe and a peripheral module include a power-storage in order to allow them to be mobile and to perform their various control and transfer functions while detached from a power-source. In some embodiments the syringe, or a peripheral module, or both the syringe and its peripheral have wireless networking in order to allow them to be externally directed or to exchange process control information while physically detached from external wiring.

In some embodiments the vessel of the peripheral module is a cuvette. In some embodiments a fluid transfer system includes a vessel that includes a barcode, a quick response code (QR code), a fiducial marker, or a near field communication tag (NFC tag). In some embodiments the vessel is an electroporation cuvette. In some embodiments the vessel comprises a cap that is fitted with at least one port. The at least one port may be automatically connected and/or disconnected for the purpose of introduction and withdrawal of plasmids, cells, buffer, etc. The ports may be arranged such that there is no possibility of cross contamination between the various sources of plasmids, cells, buffers and syringes, as vessels are automatically cycled through the station.

In some embodiments a fluid transfer system further includes at least one second peripheral module. In some embodiments the second peripheral module comprises a fluid loading station, wherein the fluid loading station is capable of rotational and/or translational movement and is configured to be mated with the syringe to allow fluid transfer between the fluid loading station and the syringe. In some embodiments the fluid loading station comprises a loading vessel that is capable of containing a liquid. In some embodiments a fluid transfer system a second peripheral module comprises a fluid supply rig, wherein the fluid supply rig comprises one or more supply vessels capable of containing a fluid, which can be mated with the fluid loading station to allow fluid transfer between the supply vessel and the fluid loading station.

In some embodiments a fluid transfer system includes a peripheral module that comprises an analysis station. In some embodiments an analysis station comprises a spectrometer. In some embodiments an analysis station comprises a UV-VIS and/or IR light source and a detector, wherein the syringe can be rotated or translated to be positioned between the light source and the detector. In some embodiments a fluid transfer system includes a peripheral station that includes a fine-pitch, lensless imaging sensor and a collimated light source, which are capable of being used in order to estimate cell viabilities and/or cell densities in a fluid that is sampled from the syringe. In some embodiments a fluid transfer system includes a peripheral station that includes a fine-pitch imaging sensor, a broadband light source, and a diffraction grating, which are capable of being used to perform spectral analysis of a fluid that is sampled from the syringe. In some embodiments a fluid transfer system includes a peripheral station that includes a fine-pitch imaging sensor, a broadband light source, and a diffraction grating, which are capable of being used to perform hyper spectral analysis of a fluid that is sampled from the syringe. In some embodiments a fluid transfer system includes a peripheral station that includes an imaging device from which data may be obtained and used to perform one or more analytical techniques selected from Partial Least Squares Regression, Gaussian Process Regression, and Support Vector Machines to estimate one or more process parameters selected from cell viability, cell density, and titer of target compounds. In some embodiments a fluid transfer system includes a peripheral station that includes a fluorescence detector, which is capable of collecting data that can be used to estimate process parameters selected from cell viability, cell density, and titer of target compounds for organisms that express fluorescent markers.

In some embodiments a fluid transfer system includes a peripheral module comprising a centrifuge that includes a centrifuge vessel capable of containing a fluid, wherein the fluid loading station can be rotated or translated to mate the loading vessel with the centrifuge vessel to allow fluid transfer between the loading station and the centrifuge. In some embodiments a fluid transfer system includes a peripheral module comprising a centrifuge, wherein the centrifuge is configured to be rotated or translated to mate the loading vessel with the centrifuge vessel to allow fluid transfer between the loading station and the centrifuge. In some embodiments a fluid transfer system includes a waste station, wherein the fluid loading station can be rotated or translated to mate the fluid loading station with the waste receptacle to allow fluid transfer between the loading station and the waste station. In some embodiments a fluid transfer system includes a waste station, wherein the waste station can be rotated or translated to mate the waste station with the fluid loading station or transfer carousel to allow fluid transfer between the fluid loading station or transfer carousel and the waste station. In some embodiments a fluid transfer system includes a chromatography rig, wherein the fluid loading station can be rotated or translated to mate the fluid loading station with the chromatography rig to allow fluid transfer between the loading station and the chromatography rig. In some embodiments a fluid transfer system includes a chromatography rig, wherein the chromatography rig can be rotated or translated to mate the chromatography rig with the fluid loading station or transfer carousel to allow fluid transfer between the fluid loading station or transfer carousel and the chromatography rig.

In some embodiments a fluid transfer system includes a peripheral station that can assemble a DNA sequence from a plurality of modular parts according to an encoded plan. In some embodiments a fluid transfer system includes a peripheral module that includes an electroporation system. In some embodiments the fluid transfer system includes a peripheral station that is capable of transforming or transfecting a target organism with the assembled DNA sequence for the purposes of creating a novel organism. In some embodiments the encoded plan is conveyed dynamically to the peripheral station via a computer network.

In some embodiments a fluid transfer system includes a peripheral module that includes a first housing comprising a first fluid reservoir and a second fluid reservoir, and a second housing concentric with the first housing, the second housing comprising a third fluid reservoir and a fourth fluid reservoir, wherein the second housing is capable of rotating relative to the first housing from a first position to a second position such that the third fluid reservoir is aligned with the first fluid reservoir in the first position and the fourth fluid reservoir is aligned with the first fluid reservoir in the second position. In some embodiments the peripheral module further includes a receiving reservoir, the receiving reservoir capable of being in fluid connection with a fluid reservoir of the first or second housing. The peripheral module may also include a safety interlock.

In some embodiments a syringe, which may form part of a fluid transfer system, includes a smart plug. In some embodiments a fluid transfer system may include a spectrometer. In some embodiments a smart plug may include a spectrometer. The smart plug may include one or more valves. The smart plug may include two electrodes. In some embodiments where a smart plug includes two electrodes, the smart plug is capable of electroporation. The smart plug may include a probe capable of measuring cellular density of a fluid contained in the syringe. In some embodiments a fluid transfer system may further include a monochromatic light source (e.g. a light emitting diode), wherein the monochromatic light source and a probe together are capable of measuring cellular density of a fluid contained in the syringe. In some embodiments a fluid transfer system may further include a wide band light source and a dispersive element, wherein the wide band light source (e.g. a tungsten lamp), dispersive element, and probe together are capable of measuring cellular density of a fluid contained in the syringe. The smart plug may include a probe capable of a capacitive measurement.

The present invention also provides for methods of transferring a fluid. In some embodiments a method of transferring fluid includes loading a fluid in a peripheral module; mating a syringe with the peripheral module to form a connection through which fluid can be exchanged, wherein the syringe is connected to a transfer carousel; drawing the fluid from the peripheral module into the syringe; rotating or translating the transfer carousel and optionally translating the syringe relative to the transfer carousel to align the syringe with a loading station; mating the syringe with the loading station to form a connection through which fluid can be exchanged; and ejecting fluid from the syringe into the loading station. In some embodiments the fluid may include a cell material.

In some embodiments a method of transferring a fluid can further include adding genetic material to the cell material in a peripheral module (e.g. electroporator or transfection station) under conditions sufficient to transfect the cell material; transfecting the cell material to form transfected cell material; and allowing the transfected cell material to incubate in the syringe.

In some embodiments a method of transferring a fluid can further include rotating or translating the loading station to align the loading station with a second peripheral module; mating the loading station with the second peripheral module to form a connection through which fluid can be exchanged; and ejecting fluid from the loading station into the second peripheral module.

The present invention also provides for methods of mixing biological inputs. In some embodiments a method of mixing biological inputs includes providing a first fluid comprising a biological material in a first reservoir of a first housing component and a second fluid comprising a biological material in a second reservoir of the second housing component; aligning the first reservoir with a receiving reservoir to form a fluid connection between the first reservoir and the receiving reservoir; dispensing the first fluid into the receiving reservoir; aligning the second reservoir with the receiving reservoir to form a fluid connection between the second reservoir and the receiving reservoir; dispensing the second fluid into the receiving reservoir; and mixing the first fluid with the second fluid in the receiving reservoir. In some embodiments the second housing further comprises a third reservoir containing a third fluid comprising a biological material, the method further comprising rotating the second housing component relative to the first housing to align the third reservoir with the receiving reservoir to form a fluid connection between the third reservoir and the receiving reservoir; dispensing the first fluid into the receiving reservoir; dispensing the third fluid into the receiving reservoir; and mixing the first fluid with the third fluid in the receiving reservoir. In some embodiments a method of mixing biological inputs further includes multiplexing the mixture of the first biological input and the third biological input. In some embodiments a method of mixing biological inputs further includes multiplexing the mixture of the first biological input and the fourth biological input. Multiplexing may be used to combine inputs for the sake of, for example, subsequent electroporation, heating, or sonication.

The present invention provides for a syringe kit, which includes a syringe body comprising a tubular body; a threaded plunger; a drive screw; and a smart plug. In some embodiments the smart plug comprises a valve. In some embodiments the smart plug comprises two electrodes. In some embodiments the smart plug comprises a probe capable of measuring cellular density of a fluid contained in the syringe. In some embodiments the syringe kit further includes a monochromatic light source, wherein the monochromatic light source (e.g. a light emitting diode) and probe together are capable of measuring cellular density of a fluid contained in the syringe. In some embodiments the syringe kit further includes a wide band light source (e.g. a tungsten lamp) and a dispersive element, wherein the wide band light source, dispersive element, and probe together are capable of measuring cellular density of a fluid contained in the syringe. In some embodiments the smart plug probe is capable of a capacitive measurement.

BRIEF DESCRIPTION OF THE SEVERAL VIEWS OF THE DRAWINGS

The foregoing summary, as well as the following detailed description of embodiments of the fluid transfer system, will be better understood when read in conjunction with the appended drawings of an exemplary embodiment. It should be understood, however, that the invention is not limited to the precise arrangements and instrumentalities shown.

In the drawings:

FIG. 6A is a plan view of an aspect of an electorporator peripheral module in accordance with an exemplary embodiment of the invention.

FIG. 6B is an elevation view of an aspect of an electorporator peripheral module in accordance with an exemplary embodiment of the invention.

FIG. 6C is an elevation perspective view of an electorporator peripheral module in accordance with an exemplary embodiment of the invention.

FIG. 8 is an orthogonal view of a fluid transfer system in accordance with an exemplary embodiment of the present invention.

DETAILED DESCRIPTION OF THE INVENTION

Figure 1:
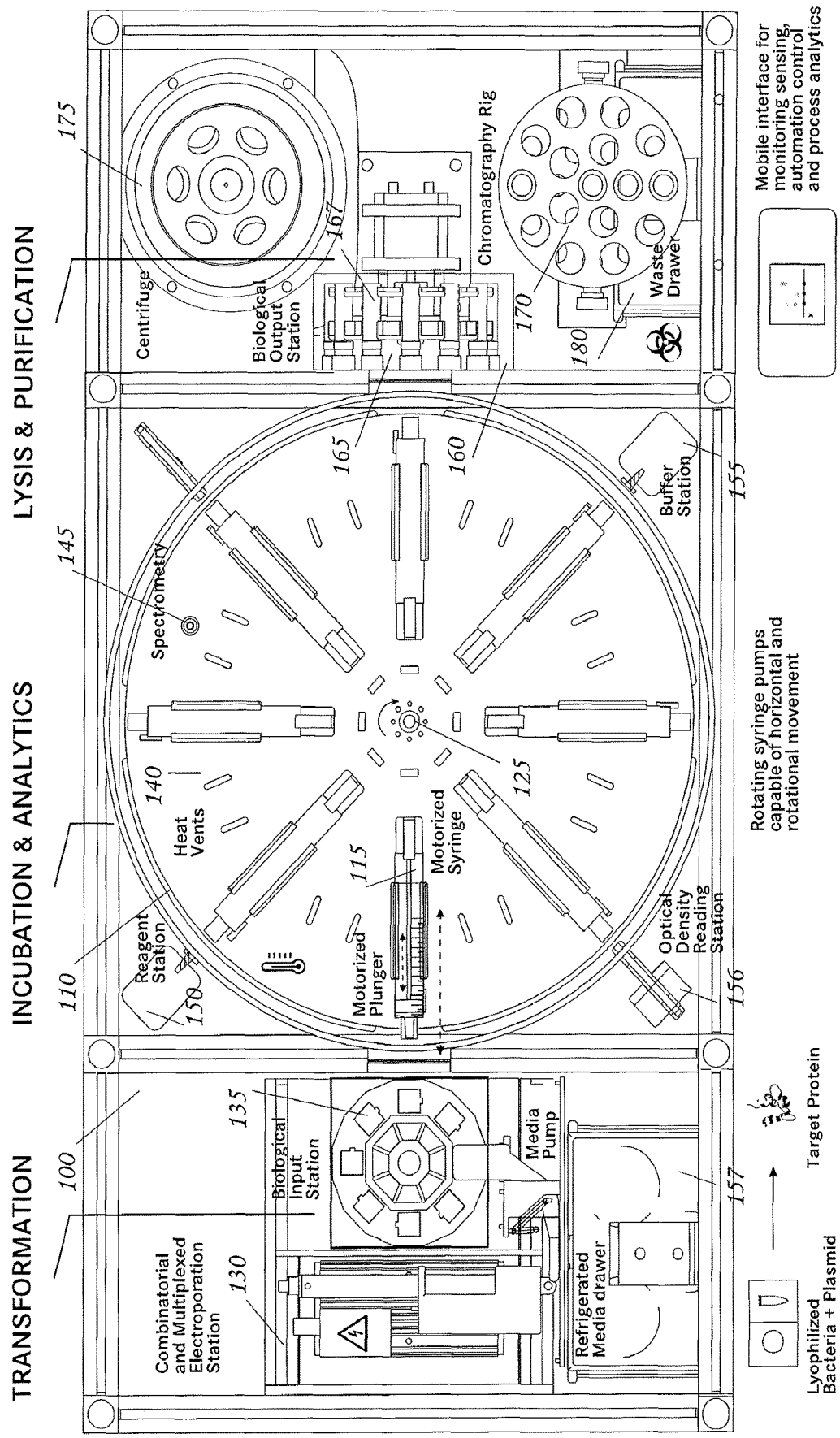
FIG. 1 is an plan view of a fluid transfer system in accordance with an exemplary embodiment of the present invention.

While the culturing of genetically modified cells is remarkably sophisticated, it is also traditionally a largely manual process. Commercial cell culture facilities do automate the cell culture process to a certain extent, but only certain aspects of the process are automated, and even this limited degree of automation tends to be prohibitively expensive.

In order to provide some perspective on the steps involved in the current state of the art, we will provide a representative description of one of the simpler use cases for genetically modifying a bacterium and culturing it in order to obtain a protein of interest. The scenario has the following steps:

Transfection—The culture of a genetically modified organism (GMO) typically begins with the step of transfection, in which a target DNA is introduced into host bacteria via a vector (i.e., plasmid) so that the bacterial culture can express a target protein. Electroporation is one method of introducing gene-carrying vectors (i.e., plasmids) into bacteria. The basic process involves mixing bacteria and plasmids together and then subjecting the mix to a brief, high-voltage pulse. The pulse disrupts the cell membrane of the bacteria, which permits the plasmids to enter within a brief amount of time (e.g., 1-4 ms). It is worth noting that the bacteria must be specially prepared such that they are electrocompetent (i.e. able to survive the electroporation process).

Recovery—Because electroporation is traumatic for the cells, electroporated cells are generally transferred to a special recovery medium and permitted to recover and grow undisturbed for a time.

Selection—Since the transfection process is an indeterministic process, some of the bacteria will have successfully taken up the plasmid DNA whereas others will not. Bacteria that are unable to express the target protein must be eliminated from the culture, since they will compete with the modified bacteria (and may, in fact, out-compete them). In order to ensure that the culture has only bacteria of interest, it is necessary to selectively cull bacteria that lack the desired genetic modifications. This is typically done by engineering the plasmid such that it not only causes the bacteria to express a target protein, but also causes them to be resistant to various selection agents (e.g. antibiotics) as well through the inclusion of a marker gene. The unmodified bacteria can therefore be easily eliminated by transferring transfected, recovered cells to a medium that contains a suitable selection agent. This selection agent will eliminate any unmodified cells, and the surviving cells will consist almost exclusively of descendants of cells that were successfully modified in the transfection stage.

Culture—Cells are typically transferred to a culture vessel in order to grow the population. The objective is to have as large a population as is attainable, since "more cells" generally means "more target protein." In principle, the culturing process is simple; we want to keep the cells nourished and in a controlled climate. For most organisms that are typically used in cell culture, "Controlled Climate" translates to keeping the cultures warm (e.g. 37° C.) and sufficiently oxygenated. If the cells are grown in a liquid medium, "sufficient oxygenation" generally involves having a sufficiently large surface area in the liquid and agitating that liquid enough to maintain adequate $O_2$ tension in the medium.

It is worth noting that cell cultures may require some analytics and some interventions. For example, we may want to monitor population density and culture viability. If the population is reaching stationary phase (i.e. no longer doubling) and if the culture has too many waste products in it, then we may use that data as a way to decide that it is time to harvest the culture. On the other hand, if we see that the population is reaching stationary phase and that the nutritive (e.g. glucose) levels in the culture are below target, then we might use that information to determine that it is necessary to add more growth medium to the culture. This introduces the interrelated notions of analytics and interventions Analytics—Analytics are used to measure selected aspects of the cell culture (population density, viability, $O_2$ tension, nutritive levels, $CO_2$ tension etc.)

Interventions—Interventions are actions taken upon the cell culture, often in response to measurements that are produced by analytics. Interventions might include medium addition, nutrient addition, gas exchange (to control $O_2$ and $CO_2$ concentrations), sample acquisition (for analytics) etc.

It is also worth noting that typical analytics are often invasive and cumbersome, since they typically require access to the culture via a port. Since physical access to the culture raises the risk of contamination (in the form of destroying the monoxenic culture or allowing a GMO organism to escape into the wild) the access protocols often have sterilization requirements that complicate the process.

Separation from Growth Medium—Once the culture has reached its endpoint, it is generally harvested. In a typical process, harvesting involves a centrifugation operation to separate cells from the growth medium in preparation for the lysation step.

Lysation—Lysation involves the mechanical or chemical reduction of cells so that they are broken into constituent parts (fragments of cell walls, cell membranes, organelles, etc.). The material that results from the lysation step is referred to as lysate. This is typically accomplished by mechanical shearing, sonication, enzymatic lysation, lyophilization followed by mechanical reduction of the dry matter, etc. The objective is to rupture the cells and reduce their constituent parts to small fragments, so that any encapsulated proteins of interest are released. In addition, the lysation operation generally reduces the cultured material in such a way that it is rendered nonviable and noninfectious.

Separation/Filtering—A separation operation often follows lysation. The intent is generally to consolidate the lysate in preparation for subsequent purification.

Purification—The objective of purification is to isolate a pure form of the target molecule. Purification can be relatively simple, or it may involve multiple steps of chemical transformation and isolation of fractions etc. The dominant tool for purification is chromatography.

Subsequent Processing—Sometimes additional processing may be required, depending on the objectives of the process. For example, some proteins need a subsequent glycosylation step in order to function properly In many settings, nearly all of these complex steps are performed by hand, In other settings, the steps may be partially automated, but the automation equipment is usually highly specialized from that standpoint that it can automate its specific portion of the process, but generally does so without regard to related steps in the process and without regard to the overall objectives of process. In addition, cell culture automation equipment is usually expensive.

In nearly all cases of current state of the art for cell culture, there is substantial human interaction with the culture at multiple points in process. Because the work is generally performed by highly-skilled individuals, and because even the most skilled individuals have limited time, limited capacity for attention and work with limited speed, there are significant constraints on the number of cultures that can be successfully managed in a given amount of time. Furthermore, such interactions inevitably involve a person "entering" the culture space in some fashion (e.g. by opening a container, reaching in with a sample syringe etc.), and each such interaction introduces some risk of contamination and/or loss of containment.

The prior art "many transfer, many interventions" practices give rise to materials and methods that limit scalability by: consuming a great deal of glassware, consuming a great deal of disposable material, requiring time-consuming and menial work by skilled personnel, etc. Together, these factors impose space, time and cost constraints that severely limit the overall throughput and the breadth of culture types that can be addressed in a given setting.

Referring to the drawings in detail, wherein like reference numerals indicate like elements throughout, there is shown in FIG. 1 a fluid transfer system 100, generally designated, in accordance with an exemplary embodiment of the present invention. Additional three-dimensional renderings of an embodiment of the invention may be found in FIGS. 8-12.

Fluid Transfer System

Referring to FIG. 1, a fluid transfer system comprises a transfer carousel 110; at least one holding vessel (e.g. a syringe) 115 that is connected to the transfer carousel 110 (also referred to herein as a culture platform), a drive motor 125 connected to the syringe 115; and a peripheral module 130 comprising at least one fluid vessel 135. In some embodiments the holding vessel may be a culture vessel and in some embodiments a culture vessel may be a syringe. Throughout this disclosure where syringe is used to describe a particular embodiment, it is to be understood that in another embodiment a different type of holding vessel or a vessel with custom liquid dispensing apparatus may be used.

In some embodiments a fluid transfer system may be a closed system wherein a fluid material introduced into peripheral module 130 can be processed and reduced to a final form without external interaction, or without being handled by a human. In other embodiments a fluid transfer system may be an open unit (also referred to herein as a non-closed system) that requires external interaction. In some open units, the fluid transfer system can operate autonomously, but may also permit intervention at the discretion of users, e.g. for removal of analytical samples and the like.

Transfer Carousel

Still referring to FIG. 1, in some embodiments the transfer carousel 110 is capable of rotational and/or translational movement. The transfer carousel may include a motor, for powering the movement of the transfer carousel. The transfer carousel may also include a driver for controlling the movement of the transfer carousel. In some embodiments at least one syringe 115 is connected to the transfer carousel 110. In other embodiments any number of syringes 115 may be connected to the transfer carousel, including 2, 3, 4, 5, 6, 7, 8 (as shown in FIG. 1), or greater than 8 syringes 115. In some embodiments all syringes 115 are positioned in a single plane, as shown in FIG. 1, while in other embodiments syringes 115 may be positioned in three dimensions, including spherically or cylindrically about the transfer carousel 110.

The at least one syringe 115 may be connected to the transfer carousel 110 such that the movement of the transfer carousel 110 results in movement of the syringe 115. The at least one syringe 115 may also be capable of translational movement relative to the transfer carousel 110. The transfer carousel can be rotated and/or translated to move the syringe 115 to be mated with the peripheral module 130 or positioned to be mated with the peripheral module 130. Syringe 115 can be moved relative to transfer carousel 110 to mate syringe 115 with peripheral module 130. In some embodiments, peripheral module 130 may comprise one or more fluid vessels 135. When syringe 115 is mated with peripheral module 130, a connection is formed between syringe 115 and fluid vessel 135 such that fluid can be exchanged between the syringe 115 and the fluid vessel 135. The connection between syringe 115 and fluid vessel 135 can be fluid tight so that while fluid can be exchanged between the fluid vessel 135 and syringe 115, the fluid does not leak to outside of the connection (e.g. using a Luer Lock or similar device). The transfer carousel 110 can also rotate and/or translate so that syringe 115 is moved to a second, third, etc. position. The transfer carousel 110 can be moved, and in particular rotated, to agitate fluid content within syringe 115. The driver and motor can be used to control the speed at which the transfer carousel is rotated and/or translated. The driver and motor can also be used to control the direction in which the transfer carousel is rotated and/or translated.

Holding Vessel

Still referring to FIG. 1, in some embodiments, a holding vessel (e.g. syringe 115, or other vessel with similar dimensions, such as a test tube) includes a tubular body 117, an opening at a first end 118 of the tubular body 117, a plunger 120, and a drive motor 125 that is capable of controlling the position of the plunger within the tubular body 117 of syringe 115. Movement of the plunger 120 within the tubular body 117 allows fluid to be withdrawn into the tubular body 117 or ejected from tubular body 117 through the opening at the first end 118. The drive motor allows the plunger 120 to be controlled accurately and precisely. Such control over the plunger 120 results in improved fluid control with reduced waste relative to manual control of a plunger. In some embodiments syringe 115 may be disposable; in other embodiments syringe 115 may be reuseable.

In some embodiments syringe 115 may be any commercially available syringe. In some embodiments the syringe-like culture vessel uses a rolling diaphragm, which in some embodiments may be a disposable item.

In some embodiments the holding vessel may be in the general form of a standard syringe which can admit or expel fluid via integrated, motorized control of the syringe plunger. Accordingly, in some embodiments a holding vessel or syringe may include a plunger drive mechanism that passes through the plunger. By passing the plunger drive mechanism through the plunger, the overall dimensions of the syringe (e.g. automated syringe) may be kept close to the overall minimal dimensions of a conventional syringe.

In some embodiments syringe 115 may be smaller than a commercially available syringes. A small dimension of syringe 115 allows a greater number of syringes 115 to be connected to the transfer carousel, which may allow a greater number of fluid samples to be processed in the fluid transfer system. A small dimension of syringe 115 may also allow the fluid transfer system as a whole to be smaller, and useful as a desktop or portable device. In some embodiments syringe 115 holds a minimum of about 1 mL, 2 mL, 5 mL, 10 mL, or about 20 mL of liquid. In some embodiments syringe 115 holds a maximum of about 100 mL, about 50 mL, about 20 mL, about 10 mL, about 5 mL, or about 1 mL (min) of liquid. However, it is foreseen that the different embodiments of the platform can utilize different vessel sizes for different applications.

In some embodiments a holding vessel (e.g. a syringe) may include a drive motor. In some embodiments the drive motor may be housed partially or fully within the body of the syringe in order to make an automated syringe whose overall dimensions are smaller than the overall minimal dimensions of a conventional syringe.

In some embodiments a holding vessel (e.g. a syringe) may be a commercially available, disposable syringe, and may include an integrated, motorized control (e.g. drive motor) for the plunger, wherein the motorized control has been designed to be retrofitted to the disposable syringe.

In some embodiments a drive motor controls plunger 120 within about +/−5% accuracy, about +/−2% accuracy, or about +/−1% accuracy. Higher precision liquid displacement solutions can be implemented by reconfiguring plunger control with additional components.

Figure 2A:
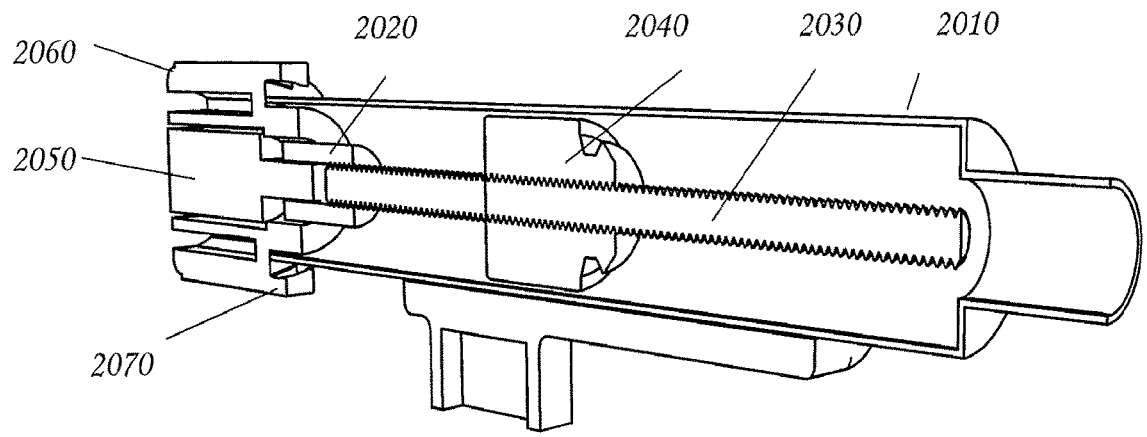
FIG. 2A is a perspective cut-away view of a holding vessel in accordance with an exemplary embodiment of the invention.
Figure 2B:
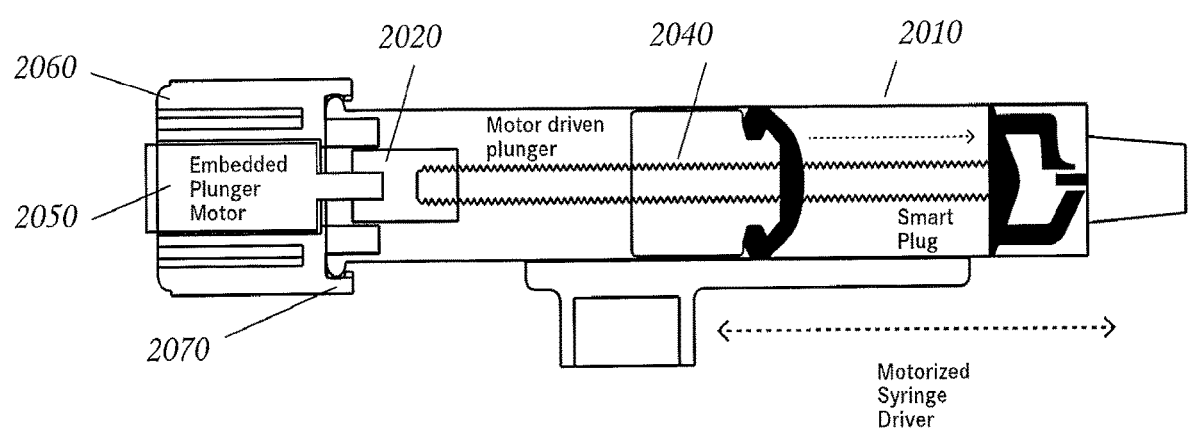
FIG. 2B is a side cut-away view of a holding vessel in accordance with an exemplary embodiment of the invention.

Referring now to FIG. 2, in some embodiments a holding vessel 2010, e.g. a syringe, contains a drive assembly comprising a drive coupler 2020 that is mated to a rod 2030 that passes through a plunger body 2040. In some embodiments the rod 2030 and plunger body 2040 are threaded. The threaded rod may be rotated by a small gear motor 2050 whose attitude with respect to the syringe may be maintained by a motor mount 2060. The motor mount may be affixed to the syringe by "tangs" 2070 that grasp the syringe, and simultaneously prevent the body of the motor from rotating, or being pushed out of the syringe.

In some embodiment the rotational mechanical advantage of any frictional force applied by the syringe wall against the plunger is much greater than that of any rotational frictional force applied by the threaded rod against the interior of the threaded plunger. Accordingly, in such embodiments there is little or no tendency for the plunger to rotate in response to rotation of the threaded rod. As a result, when the threaded rod is rotated, the plunger may move readily along the threaded rod's axis, thereby altering the interior volume of the syringe. In some embodiments, the plunger can be explicitly prevented from rotating using one or more of a variety of mechanisms, such as an embedded magnet that is attracted to a steel bar under the syringe, or embedded splines in the plunger that counter rotation, yet freely permit axial movements, etc.

In some embodiments, with a suitable choice of materials, the threaded rod turns relatively freely within the plunger, yet forms a fluid-tight seal. The ridges at the interface between the threaded rod and interior plungers may create a long channel that has enough fluidic resistance to prevent leakage, even when the fit is less than ideal. In some embodiments, this fluid-tightness can be augmented using suitable, one or more chemically inert lubricants, such as silicone vacuum grease.

In some embodiments the syringe drive motor 2050 is under computer control. In an exemplary embodiment, the motor is quadrature encoded and the system is capable of controlling the syringe volume with remarkable precision (e.g., +/− ca. 1 microliters, 2 microliters, 5 microliters, or 10 microliters) for any volume between 0 and 8000 microliters.

In some embodiments, a holding vessel (e.g. a syringe) may include instrumentation, for example analytical instrumentation, that is embedded in the plunger for the sake of monitoring the contents of the syringe. In other embodiments the holding vessel may include external instrumentation, for example analytical instrumentation, that is attached to the outside of the syringe body. In some embodiments external instrumentation may define a ring (e.g. a sensor ring), which encircles the holding vessel. Some examples of analytical instrumentation include optical density sensors and NMR sensors. In some embodiments the instrumentation may be miniaturized.

Referring to FIGS. 3, 4A, 4B, 5A, and 5B, in some embodiments a holding vessel, (e.g. a syringe), may comprise a "smart plug". As used herein, the term "smart plug" refers to any functional element that is within the body of the syringe, e.g. a special valve, an optical density reader, a capacitive sensor, etc., that is capable of providing analytical data regarding the contents of the syringe. In some embodiments, such mechanisms can be fitted into a specialized plunger mechanism in the holding vessel.

Figure 3A:
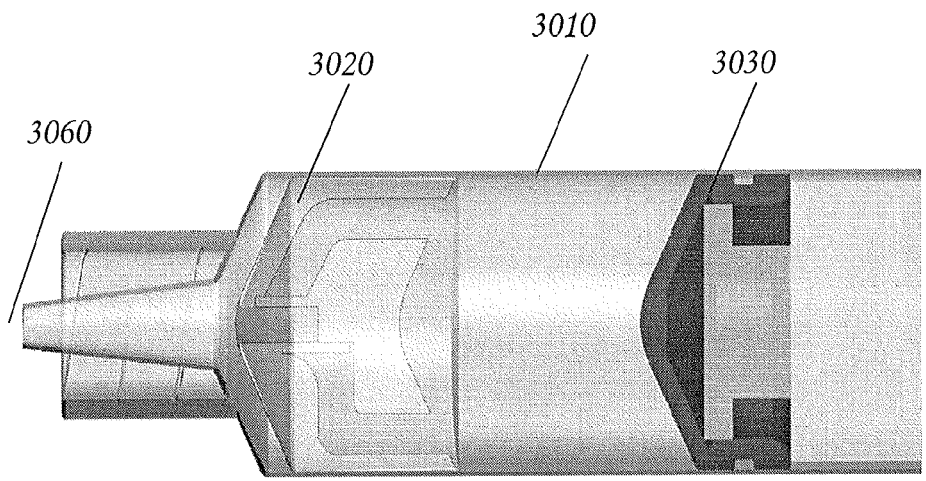
FIG. 3 is a side view of a holding vessel in accordance with an exemplary embodiment of the invention.
Figure 3B:
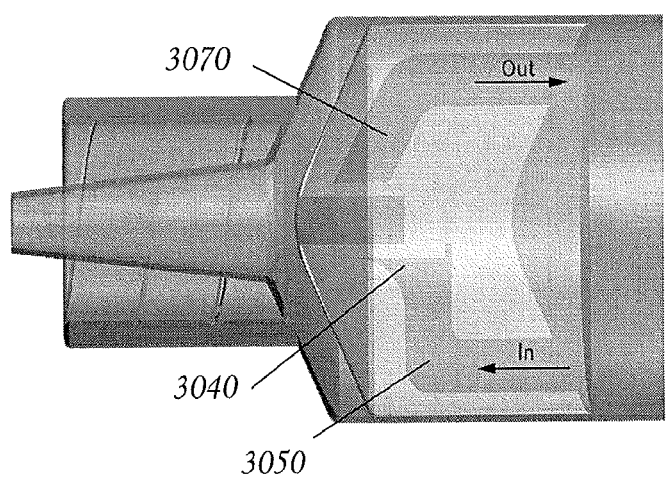

Referring to FIG. 3, in some embodiments, a syringe 3010 is fitted with a plug 3020 that is made of compliant material, such as polydimethylsiloxane polymer (PDMS). In some embodiments, when the syringe plunger 3030 is drawn away from the syringe, the interior pressure drops and causes the lower check valve 3040 to open, thereby admitting fluid to the interior of the syringe via the lower passage of the plug 3050. If the syringe tip 3060 is open to the air and there is a liquid culture in the syringe, this action may cause air to bubble through the culture, thereby aerating it. If the interior volume of the syringe is somewhat greater than the volume of the liquid culture, a gas-filled head-space may form at the top of the syringe. In some embodiments, this space will accumulate respiration byproducts (typically dominated by $CO_2$ in aerobic cultures, or by $H_2$ or methane in anaerobic cultures). Advancing the plunger towards the syringe tip may cause the interior pressure of the syringe to increase, thereby in some embodiments opening the upper check-valve 3070 and permitting fluid to exit the syringe. When there is sufficient headspace in the syringe, this fluid may comprise a gas that includes respiration byproducts. In some embodiments this check valve scheme can also be used to vent respiration gasses if their pressure rises above ambient air-pressure, while at the same time preventing culture fluid from being forced out. In some embodiments, in the absence of a gas head-space, the valve assembly acts essentially like an "unvalued" syringe. In some embodiments the valve can function as a decantation mechanism and be used to separate any immiscible fluids of dissimilar density that happen to be in the syringe.

Figure 4A:
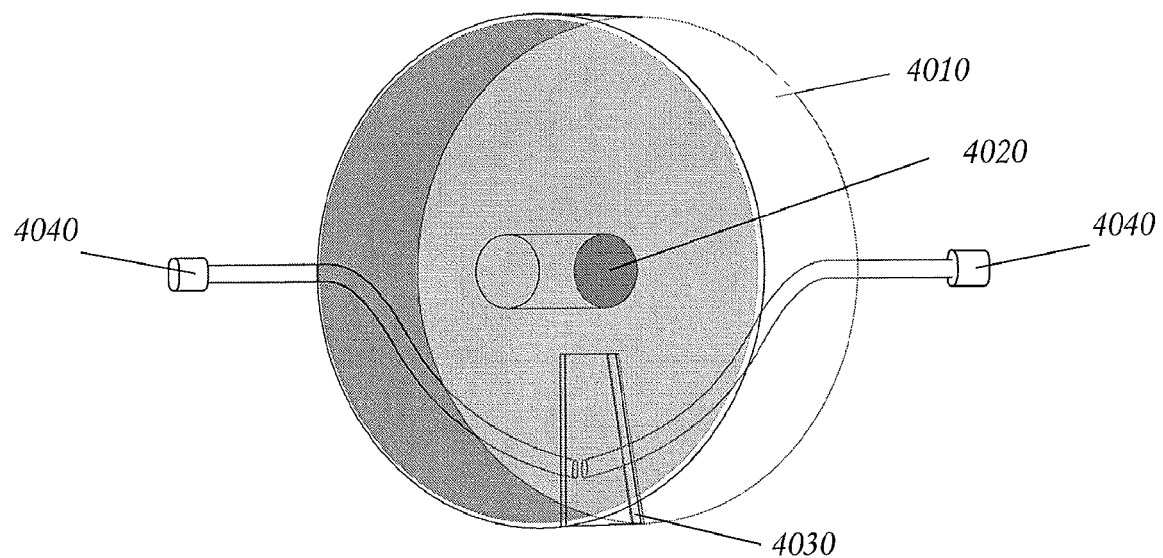
FIG. 4A is a perspective view of a smart plug in accordance with an exemplary embodiment of the invention.
Figure 4B:
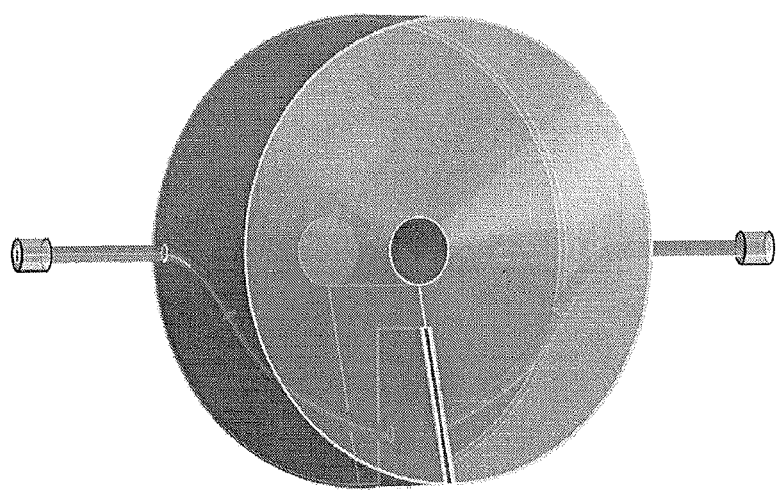
FIG. 4B is a rendered view of the smart plug shown in FIG. 4A.

Referring to FIGS. 4A and 4B, in some embodiments a "smart-plug" electroporation mechanism comprises a plug body 4010, which may be designed to occupy, for example, the first ½ cc (or the first 1 cc, 2 cc, 3 cc, 4 cc, 5 cc or more) of a standard syringe (e.g. 10 cc syringe) (not shown), and which has a passage 4020 through the plug body (e.g. the center of the plug body), which allows the syringe to function normally. Below this passage is a narrow slot 4030 with small, parallel metallic plates on the opposite faces of the gap. These plates may be separated by a narrow gap (e.g. 0.1 to 0.3 mm). The plates may each be attached to electrodes 4040 that pass through opposite sides of the syringe wall. Accordingly, a small volume of fluid containing cells and plasmids can be introduced between the two plates, and the cells can be electroporated via an electrical pulse, which drives plasmids into some of the cells, and thereby transforms them genetically. In some embodiments the separation between the gaps in this mechanism are approximately ¹/₁₀th as wide as gaps used in standard electroporation cuvettes, thereby permitting the use of much lower voltages for electroporation. This gives the electroporator significant advantages in terms of cost, simplicity, compactness and safety, and it eliminates the need to transfer material from an external electroporation cuvette, further simplifying the system design. The combination of safety, simplicity and low cost will favor the use of micro-electroporation mechanisms over larger, high-voltage transformation mechanism in some cases. In some embodiments there are specialized low voltage electroporation methods, such as methods that use microporous membranes to greatly increase the electric field around a transformant organism that could be easily integrated into a "smart plug" form similar to that shown in FIGS. 4A and 4B.

Figure 5A:
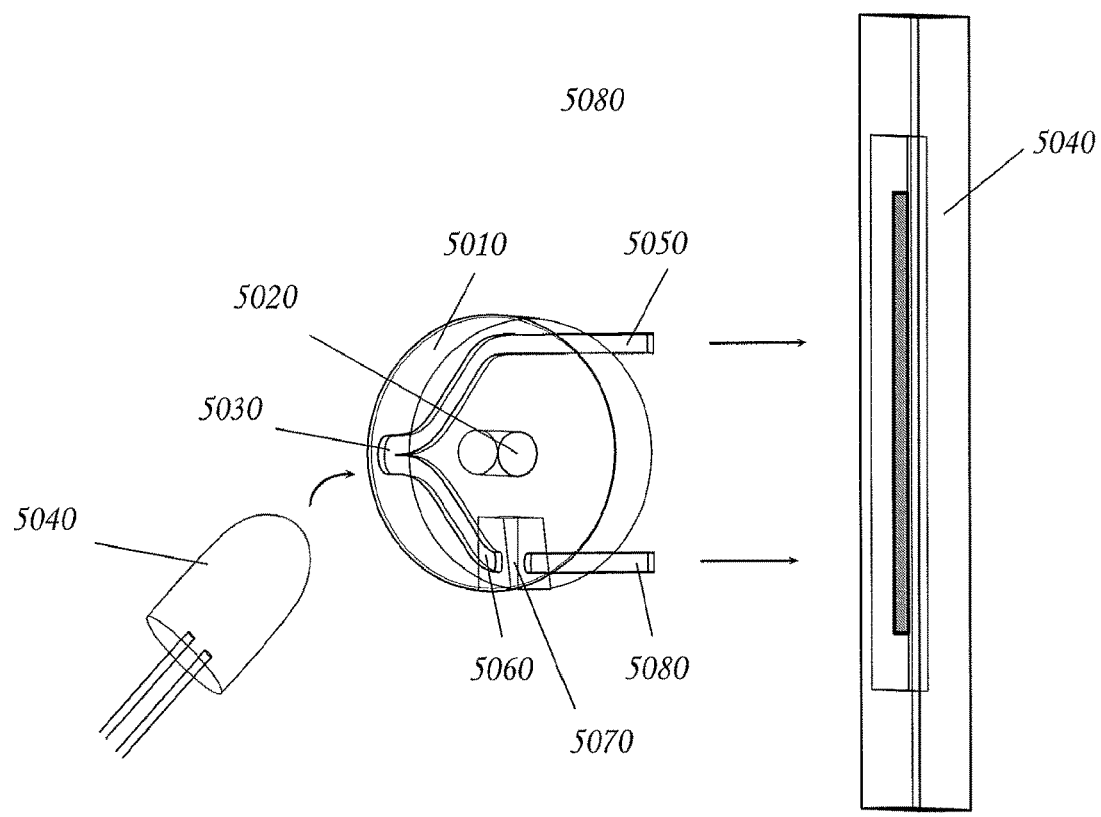
FIG. 5A is a perspective view of a smart plug in accordance with an exemplary embodiment of the invention.
Figure 5B:
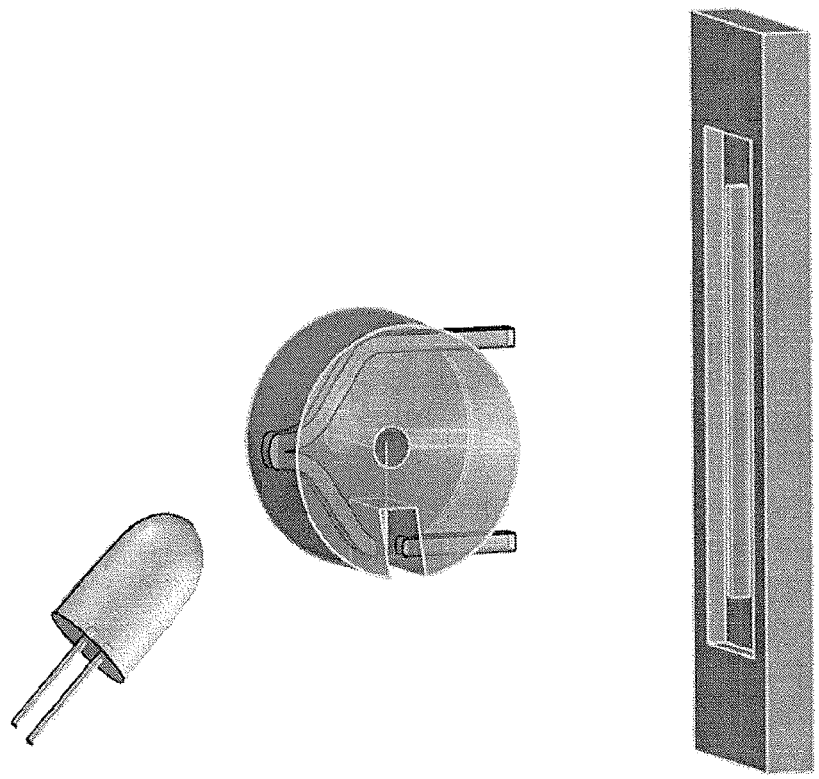
FIG. 5B is a rendered view of the smart plug shown in FIG. 5A.

FIGS. 5A and 5B shows an embodiment of an optical density "smart plug." In this particular example, the heart of the device is a plug-like body 5010 that occupies for example, the first ½ cc (or the first 1 cc, 2 cc, 3 cc, 4 cc, 5 cc or more) of a standard syringe (e.g. 10 cc syringe). This plug features a passage 5020 that permits the syringe to operate normally. Within this plug body is a light-pipe (5030) that splits incident light from an illumination source 5040 into an upper-path 5050 and a lower path 5060. Light from the lower-path may be directed across gap 5070. This gap may be oriented within a liquid culture vessel such that it is at the bottom, and therefore immersed in the liquid culture (not shown). Light incident on the first side of the gap may be received on the opposite side by a second light pipe 5080. Light emerging from the upper and lower paths may be imaged onto a charge coupled device (CCD) array 5090. A microcontroller (not shown) can be used to read the CCD array. In some embodiments, by comparing the integral of the signal generated by projection of light from the upper light path onto the CCD, relative to the signal generated by projection of light from the lower light path onto the CCD, it is possible to measure the absorbance of material in the sample gap 5070, while at the same time correcting for various possible issues (e.g. fluctuations of illumination intensity) that might arise in the system. This absorbance measurement can be scaled into a standard Optical Density ("OD") measurement, and from there cell density in a culture can be estimated. In some embodiments the system can potentially identify anomalies such as bubbles or debris within the optical path by virtue of any anomalous features in the CCD image. Thus anomalous readings could be flagged and possibly excluded from any sequence of OD measurements.

In some embodiments the mechanism of FIGS. 5A and 5B allows for a number of interesting variations. For example, the light-pipes can be molded with integrated optical elements, such as prisms, lenses and the like, thereby forming an optical system. This would permit arrangements wherein the illumination source could be a broad-band source, and the light-pipe signal could be collimated using integrated lenses and subsequently projected onto a reflective diffraction grating, or passed through a transmissive diffraction grating before being projected onto the CCD. In this case, the system would be functioning as broad-band spectrometer, which in turn opens the door to possibilities such as sophisticated, in-line analytics using multivariate analysis of resulting spectra.

In some embodiments a micro-electroporation mechanism, for example, the embodiment shown in FIGS. 5A and 5B, could double as a capacitive sensor that can be used to estimate the density and size of cells in the culture via impedance spectroscopy. In fact, the basic idea of a "smart-plug" could be readily employed as a basis for a capacitive cell density meter that is fully optimized for the task of measuring cell culture density, with ideal gap geometry, ideal electrode geometry, inclusion of counter-electrodes etc.

In some embodiments, a holding vessel (e.g. a syringe) may include one or more ports. The one or more ports may pass through the plunger and permit, for example, monitoring of gas tension in the contents of the syringe and/or control of gas tension in the contents of the syringe.

Peripheral Module (E.g. Electroporation Device)

Referring again to FIG. 1, in some embodiments, peripheral module 130 comprises at least one fluid vessel 135, wherein the fluid vessel 135 has an opening that can be mated with the syringe 115 to allow fluid transfer between the fluid vessel 135 and the syringe 115. The mating may form a fluid tight connection such that fluid exchanged between the fluid vessel 135 and the syringe 115 does not leak outside the connection. For example, such a fluid tight connection may be accomplished through the use of a Luer Lock or similar device. In some embodiments peripheral module 130 includes a plurality of fluid vessels 135, which may be moved to provide a sterile fluid vessel 135 after use of another fluid vessel 135. Such movement may be accomplished via a conveyor belt or other automated system. In some embodiments, peripheral module 130 may further include a cooling unit. In some embodiments, peripheral module 130 can be rotated or translated to mate a fluid vessel 135 with a holding vessel (e.g. syringe 115) to allow fluid transfer between the fluid vessel 135 and the holding vessel 115.

In some embodiments the syringe, or its peripheral station, or both the syringe and its peripheral station are brought together by at least one mobile platform, such as an automated robot (e.g. a Kiva robot). In some embodiments the syringe, its peripheral station, or both the syringe and its peripheral station include power storage order to allow them to be mobile and to perform their various control and transfer functions while detached from a power-source. In some embodiments the syringe, its peripheral station, or both the syringe and its peripheral station have wireless networking in order to allow them to be externally directed or to exchange process control information while physically detached from external wiring.

In some embodiments peripheral module 130 is a transfection station in which a cell material may be transfected with a genetic material. In some embodiments a transfection station is an electroporation station. Still referring to FIG. 1, peripheral module 130 is an electroporation station, and includes a pair of electrodes 132 and at least one fluid vessel that may be an electroporation cuvette 135 having a pair of cuvette electrodes 133. Each cuvette 135 in the electroporation station 130 is moved into position between electrodes 132 that make contact with corresponding cuvette electrodes. An electroporation device (not shown) may impart a brief, high-voltage pulse to the contents of the cuvette 135. This electroporation pulse may briefly open pores in the cell membranes of organisms contained within cuvette 135, and some of the plasmids will enter some of the host cells. The details of the electroporation process vary, based on the organism being transfected and various other details, and appropriate parameters and/or conditions will be understood by a person of ordinary skill in the art. Electroporation parameters can be programmed into a processor for controlling the transfection station 130. In some embodiments cuvette 135 includes a barcode, QR code, a fiducial marker, NFC tag, visual code, or other identification device to allow identification of the particular cuvette 135 and monitoring of the fluid contained therein as it is processed through the fluid transfer system 100. In some embodiments such identification is readily discernable to a human eye (e.g. color, letter, numeral, or other symbol).

In some embodiments an electroporation cuvette may include a cap that is fitted with at least one port whereby plasmids and target organisms can be individually introduced in preparation for electroporation, whereby buffer solution can be introduced after electroporation, and/or whereby electroporated cells may be withdrawn for subsequent culturing. In some embodiments at least one port may be automatically connected and disconnected for the purpose of introduction and withdrawal of plasmids, cells, buffer etc. and whereby said ports are arranged such that there is no possibility of cross contamination between the various sources of plasmids, cells, buffers and culture vessels as cuvettes are automatically cycled through the station.

Identification can be controlled by the processor and the processor may be programmed to select appropriate parameters for the electroporation pulse. In some embodiments, the discharge voltage and current of the electroporation action are monitored, so that the electroporator can ascertain whether the electroporation action was successful and can automatically discard the contents of any cuvette for which the electroporation cycle was unsuitable. In some embodiments, the discharge voltage and current of the electroporation action are monitored, and the electroporator is capable of reading the identity of a labeled cuvette 135, via a bar code, a QR code, a fiducial marker, an NFC tag, etc., and tracking the outcome of cultures that used a given electroporation profile for the sake of developing optimal electroporation profiles for given applications.

While electroporation is provided herein as one exemplary method of transfection, any transfection method known to one of ordinary skill in the art may be used, including other instrument based methods (e.g., biolistic technology, microinjection, laserfection/optoinjection, etc.), reagent based methods (e.g., use of lipids, calcium phosphate, cationic polymers, DEAE-dextran, activated dendrimers, magnetic beads, etc.), or virus based methods (e.g., retrovirus, lentivirus, adenovirus, adeno-associated virus, herpes simplex virus, vaccinia virus, etc.). Accordingly, in some embodiments, peripheral module 130 may be a reagent based transfection station comprising one or more fluid vessels. Transfection stations utilizing magnetic beads may further comprise a magnetic plate. In other embodiments peripheral module 130 may be a biolistic station comprising a fluid vessel 135 and a gene gun. In other embodiments peripheral module 130 may be a microinjection station comprising a fluid vessel 135 and an injection pipette. In some embodiments, a peripheral module 130 comprises two key features: 1) combinatorial mixing of inputs and 2) multiplexing inputs for individual treatment. The combinatorial mixing of inputs allows the selective pairing of DNA and target organisms by coupling them in different combinations such that different DNA designs can be inserted to the same organism, the same DNA can be inserted to multiple host organisms, or different organisms can be combined with each other for designing microbial ecologies. Multiplexing inputs for individual treatment allows the combined inputs to be inserted into individual cuvettes so that they can be selectively treated. In one embodiment this feature is used to selectively electroporate individual cuvettes so that different DNAs can be inserted to the targeted organisms through electricity. However, the individual treatment of the cuvettes does not have to be limited to electroporation. Different design operations can also be applied here (e.g., heat shocking, sonication, and so on).

FIGS. 6A-6C describe an embodiment of peripheral module 6000 that demonstrates the use of such system. As shown in FIG. 6A, in some embodiments two or more concentric elements (e.g., Ring A 6010 & B 6020) can rotate in opposition (e.g. clockwise and counter-clockwise), or one or more first elements that can be held stationary while one or more other elements are rotated relative to the first elements, to pair different input positions 6030a, 6030b. As shown in FIG. 6B, once a desired pairing is made, the inputs 6030a, 6030b can be pushed down inside a vessel 6040 to be treated with electricity, heat, sound, light, and so on.

As shown in FIG. 6C, in some embodiments, two or more concentric elements 6010, 6020 of a peripheral module 6000 together form the basis of an experiment design system that allows users to design biological experiments by mixing standardized inputs (e.g., nucleotide sequences, plasmids, target organisms, inhibitors, media) in different sequences and amounts. This system can explore a combinatorial design space by algorithmically generating individual pairings, which then can be automatically tested for different feasibility and optimization settings through automated culturing. The system can be based on two or more elements (e.g. rings) that can be rotated relative to each other to pair different sources of input and a dispensing mechanism that can mix the inputs inside a single vessel where they can be individually processed. An additional (e.g. third) rotational or translational mechanism 6050 then commutes these vessels to different positions where their content can be transferred to an automated culturing system.

Figure 7A:
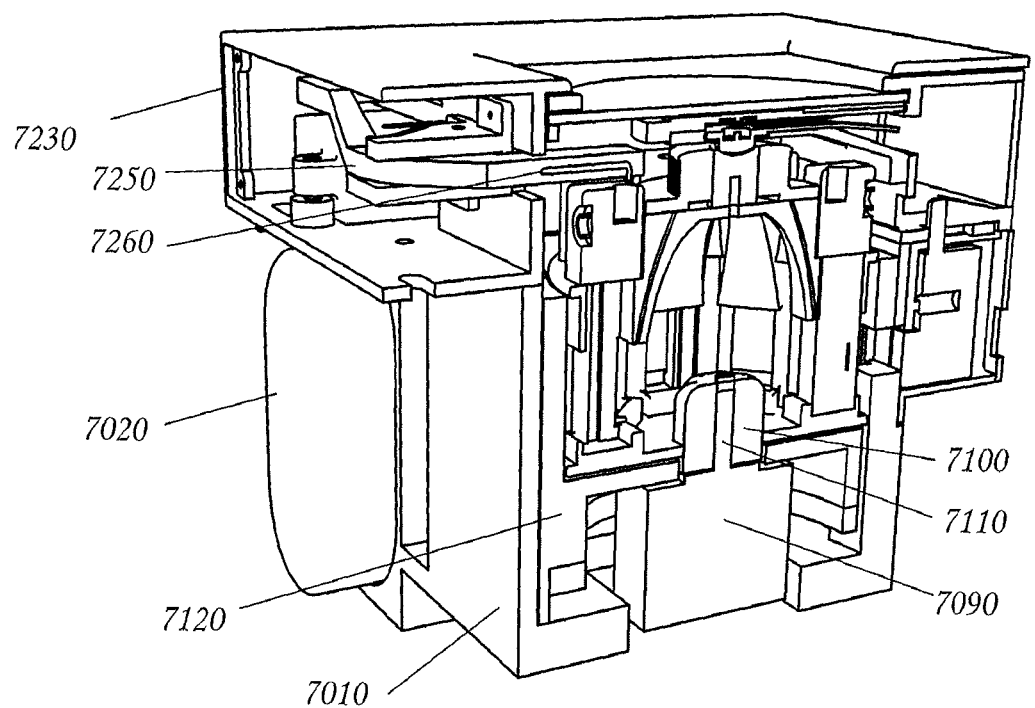
FIG. 7 is an elevation cut-away view of an electorporator peripheral module in accordance with an exemplary embodiment of the invention.
Figure 7B:
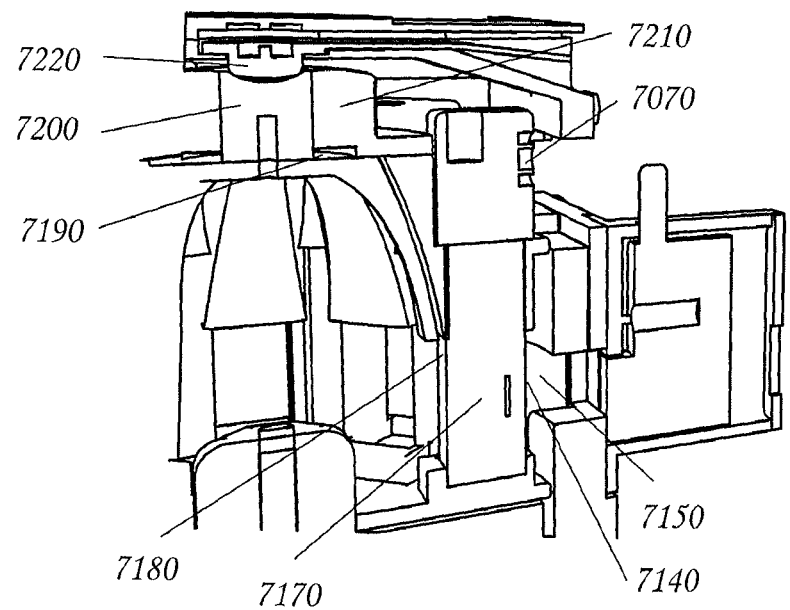
Figure 7C:
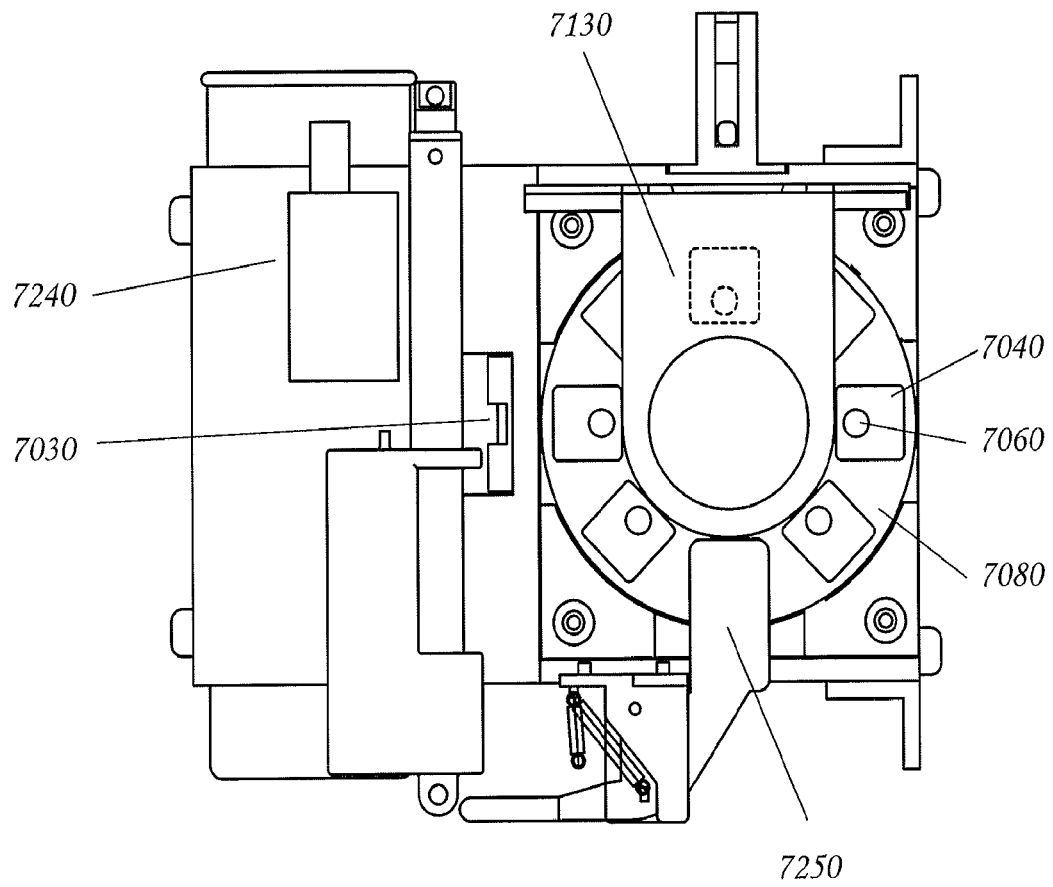

FIG. 7 shows an embodiment of an automated electroporation device that implements a rotary, commutating electroporator mechanism. The overall device may be encapsulated in a mounting bracket 7010, which supports the overall structure, and which may host a large pulse capacitor 7020 that is used discharge a high voltage pulse through a sample for the sake of electroporation. Electroporation samples may be scanned by a camera 7030 and computer vision methods may be used to ensure proper angular alignment of sample cuvettes 7040 and/or to obtain contextual information (e.g. plasmid design and host organism) via one or more 2D codes on cuvette caps (not shown). The cuvette caps may contain features (not shown) that permit them to be pre-loaded with plasmids and host organisms. Furthermore the cuvette caps may have a port 7060 for introduction of a fluid (e.g., a nutritive rich media such as SOC (Super Optimal Broth with Catabolite Repression)) and an additional port 7070 for sample withdrawal via syringe.

Controlled electroporation may be accomplished by commutation of the individual cuvettes. Still referring to FIG. 7, in an exemplary embodiment, commutation is achieved by rotation of a substantially cylindrical carousel 7080 that is rotated by a computer-controlled stepper motor 7090. The carousel is removable, and coupling between the carousel is accomplished via an octagonal nut 7100 that is connected the stepper motor shaft 7110. In this embodiment, an octagonal nut was used because the cuvette carousel is capable of hosting eight cuvettes, however any geometrically shaped nut (e.g. circular, oval, triangular, rectangular, pentagonal, hexagonal, heptagonal, octagonal, nonagonal, decagonal, dodecagonal, pentadecagonal, or icosagonal) may be used and the carousel may host any number of cuvettes (e.g. 1, 2, 3, 4, 5, 6, 7, 8, 9, 10, 11, 12, 15, or 20). In this exemplary embodiment, since the drive nut cannot be seen by a user when the carousel is being inserted, the correspondence between the number of sides of the nut (e.g. octagonal) and the number of cuvettes (e.g. eight) results in visual cueing that makes proper insertion of the carousel somewhat easier.

A stepper motor may be mounted in a "nest" structure 7120 that can, itself, be removed from the main bracket 7010. This nest may be made free-floating so that its attitude can be finely adjusted via positioning screws (not shown). Accordingly, the position of the carousel's cuvettes relative to automated syringes that withdraw cuvette contents can be adjusted with great precision, so that syringes can readily engage with the cuvette sample ports 7070 when samples are withdrawn for culture.

In some embodiments, commutation may be achieved via rotation or translation of the carousel. In some embodiments, by carefully rotating the carousel, a particular cuvette may be selected for electroporation. Referring to FIG. 7, when the selected cuvette is in the electroporation position 7130, a first aluminum electrode 7140, which may be integral to each cuvette, may be brought into contact with a brush electrode 7150, which may be connected to the first pole of the electroporation circuit. In some embodiments the cuvette has a second integral aluminum electrode 7170 that is opposite the first electrode, and separated from it by a small gap (typically 1 to 3 mm). Cell and plasmid filled fluid that is to be pulsed for electroporation is held between these two electrodes. The second cuvette electrode 7170 may be held in place against a spring electrode 7180 that maintains a firm contact with the second cuvette electrode. This spring structure may pass through a special channel in the cuvette carousel where it meets with a thin metallic strip 7190. These metallic strips may be used to make an electrical connection with a metal "cap" 7200 that is contained within the carousel's top handle 7210, and which has a shallow depression on top. In some embodiments, a spring loaded "button" 7220 drops into the shallow depression of the cap 7200 when the lid of the electroporation unit 7230 is closed. Thus, when the lid is closed, the button may be electrically connected to "cap," strip, spring, second electrode sequence below it. In some embodiments the "button" is further connected to the second pole of the electroporation pulse circuit. Therefore, in some embodiments, when the computer controlled electroporator generates a pulse between its first and second pole, the pulse travels: to the brush electrode 7150, through the cuvette first electrode 7140, through the cell and plasmid filled fluid 7160, through the cuvette second electrode 170, through the spring electrode 7180, through a metallic strip 7190, through the carousel "cap" 7200, through the spring loaded button 7220 and from there to the second pole of the electroporator.

In some embodiments, an automated electroporator may include a housing. Such housing may include a shell and/or a lid. In some embodiments, the lid of the exemplary automated electroporator has several safety features that are useful in practical implementation. Because the electrical pulses generated by an electroporator can be hazardous, or even lethal, it is useful to protect a user from any risk of inadvertently touching the electroporation circuitry when the machine is in use. However, users must also be able to easily insert samples into the electroporation mechanism for each new experiment. Accordingly, an exemplary design features physical safety interlocks. In some embodiments, when the lid is open, the spring loaded button 7220 is disengaged from the cuvette carousel. Furthermore, the button itself may be electrically disconnected from the electroporation circuitry by means of a disengagement plug 7240. Finally, the commutating brush electrode 7150 may be retracted by the mechanical action of opening the lid. This permits users to freely handle the cuvette carousel for the sake of inserting or withdrawing it when the lid is open, without any risk of shock in the event of an unexpected discharge of the electroporator.

In some embodiments, the electroporator bracket 7010, the carousel "nest" 7120, the carousel itself 7080 and the cuvette caps 7050 are all rigid structures that are designed to work together to serve an important mechanical function. In such embodiments when a syringe is inserted into the sampling port of a cuvette cap 7070, it applies a fair amount of force. This force is transmitted to the carousel 7080 due to the close fit between the back of the cuvette cap and the carousel. The carousel then transmits this force to the carousel "nest" 7120 because there is a close fit between the carousel's rim and the nest. The nest transmits the force to the main bracket, again by virtue of a tight fit, and the bracket transmits force to the frame of the overall machine structure, which is easily able to anchor the assembly against any unwanted motion. As a result of this design, in some embodiments the carousel nest is able to spin freely, which is necessary to move cuvettes between their various stations in the electroporator, but it is rigid in opposition to the pressure from inserted syringes, which is necessary to permit syringes to be inserted with sufficient force to form a fluid-tight seal.

In some embodiments the electroporator design has several features that are simply practical. For example, the mechanism may contain a fluid (e.g. a nutritive rich media such as SOC) dispensing arm 7250 that may be pushed by a cam in the electroporator lid such that the arm swings into position over a cuvette when the lid is closed. This dispensing arm may contain a fluid channel 7260 that is used to drip a fluid (e.g. a nutritive rich media such as SOC) into a port 7060 in the specially designed cuvette caps. As a result, a small, computer controlled pump (not shown) is able to quickly introduce a fluid (e.g. a nutritive rich media such as SOC) into an electroporation cuvette after an electroporation pulse has been delivered. When the lid is opened, the cam may be withdrawn and the fluid (e.g. a nutritive rich media such as SOC) dispenser arm may retract under spring tension, thereby allowing the cuvette carousel to be freely removed.

In some embodiments the electroporator includes the use of an automated, sliding lid. This approach may be advantageous because most other methods for accessing the interior of the electroporator (e.g. raising one side of a hinged lid) pose a risk in a busy lab from the standpoint that hinged lids and the like can be inadvertently hit in such a way that their hinges can be over-stressed and damaged.

In some embodiments the electroporator includes ergonomic elements. For example, referring to FIG. 7, carousel nest 7120 features a small radiused lip (not shown) that makes it significantly easier to insert the carousel into the nest. Another ergonomic design element provided in some embodiments is the shape of the holders for the electroporation cuvettes. These holders may form a close fit around the cuvettes, which holds the cuvettes rigidly in position. Furthermore, in some embodiments the holders include a small channel (not shown) on one side. This channel matches a small orienting key that all electroporation cuvettes have, and as a result, it is difficult or impossible to insert an electroporation cuvette into the carousel in an improper orientation. The guided or enforced orientation ensures that the cuvette electrodes contact the spring electrodes 7180 and the brush electrode 7150 as needed. In some embodiments the cuvette caps are designed such that the "back" of the cap, i.e. the portion opposite sample port, is the thinnest portion of the cap structure. Therefore, if the cap is improperly oriented on a cuvette, it is difficult or impossible to insert the capped cuvette into the carousel. Together, these orienting features ensure that the device is easy to use, and that is is effectively impossible to assemble the pieces in such a way that the mechanism will fail to operate properly.

In some embodiments, a peripheral module (e.g. electroporator) comprises a cooling system. For example, an electoporator may include a fluid cooling system in the housing of the automated electroporator, for example the shell of the electroporator. Such a cooling system may comprise one or more tubes capable of containing a cooling fluid. In some embodiments the one or more tubes may be integrated into the walls of the structure that surrounds the electroporation cuvettes (e.g. housing, shell). In some embodiments the peripheral module (e.g. electroporator) includes a fluid chilling system (the design of which would be apparent to one of ordinary skill in the art). In some embodiments the peripheral module (e.g. electroporator) includes insulation on the interior, exterior, or interior and exterior of the housing (e.g. shell) walls. The interior of the electroporator would then be chilled by circulating chilled fluid through the integrated tubes.

In a preferred embodiment, the use of pumps, tubes and other intermediate carriers of fluids are generally avoided in the biologically active portions of the process. The reason for this is that such devices are easily contaminated, and their presence would add considerable complexity to the design and generate considerable waste if such components were disposable. Instead, nearly all fluid transfers in the system are achieved by direct transfer between a source and destination vessel. This is done by joining ports between the source and destination vessels, and then changing the volume of the source vessel, the destination vessel, or both, in order to create a differential pressure that draws fluid from the source vessel and into the destination vessel.

Additional Components

Referring again to FIG. 1, in some embodiments, a fluid transfer system may include one or more additional components, such as one or more heat vents 140, one or more analysis stations 145 (e.g. an optical density reading station 156 that is capable of monitoring the cell growth within individual holding vessels (e.g. syringes)), one or more reagent 150 and/or refrigerated media storage drawers for media storage and dispensation (e.g. buffer stations) 155, a fluid loading station 160, a fluid supply rig 165, a chromatography rig 170, a vortex (e.g. centrifuge) 175, and/or a waste collection station 180. Other peripheral modules and/or stations that would be useful in fluid processing and/or analysis may be included in a fluid transfer system according to the invention, wherein other such peripheral module and/or station utilizes the same fluid transfer principles discussed herein and would be apparent to one skilled in the art reading this disclosure.

In some embodiments a fluid transfer system can include a peripheral module (e.g. an electroporation station) that includes one or more vessels (e.g. cuvettes). In some embodiments an electroporation station may be capable of accepting multiple vessels (e.g. electroporation cuvettes), successively electroporating the contents of each cuvette, and participating in automated exchange of electroporated contents of each cuvette such that the contents of the cuvette can be transferred to a suitable vessel (e.g. a holding vessel such as a syringe) for subsequent culture. In some embodiments an electroporation system includes cuvettes that are labeled with a code, such as bar code, a QR code, a fiducial marker, an NFC tag, etc., so that the product of the electroporation action can be traced through a fluid transfer or cell culture system, for example, via knowledge of the code associated with an individual cuvette. In some embodiments, the contents of the cuvette can be tracked products are moved through the process via transfers managed by the fluid transfer or cell culture automation system.

In some embodiments, the discharge voltage and current of the electroporation action at an electroporation station can be monitored, so that the electroporator can ascertain whether the electroporation action was successful and can automatically discard the contents of any cuvette for which the electroporation cycle was unsuitable. In some embodiments, the electroporator is capable of reading labeled cuvette identity, via a bar code, a QR code, a fiducial marker, an NFC tag etc. and tracking the outcome of cultures that used a given electroporation profile for the sake of developing optimal electroporation profiles for a given application.

In some embodiments syringe 115 may be used for incubation of a cell medium that was transfected in a transfection station 130. Accordingly, in some embodiments a fluid transfer system 100 may include one or more reagent stations 150 and/or one or more buffer stations 155. Reagent station 150 may be a vessel capable of holding a fluid and having an opening which can be mated to syringe 115 to allow for exchange of fluid between the reagent station 150 and syringe 115. The mating may form a fluid tight connection such that fluid exchanged between the reagent station 150 and the syringe 115 does not leak outside the connection. For example, such a fluid tight connection may be accomplished through the use of a Luer Lock or similar device. Similarly, buffer station 155 may be a vessel capable of holding a fluid and having an opening which can be mated to syringe 115 to allow for exchange of fluid between the buffer station 155 and syringe 115. The mating may form a fluid tight connection such that fluid exchanged between the buffer station 155 and the syringe 115 does not leak outside the connection. Reagent station 150 and/or buffer station 155 may contain any reagent, buffer, or fluid medium useful for culturing, lysing, processing, or purifying a cell culture fluid, or otherwise useful in processing a fluid to be transferred with a fluid transfer system 100.

Transfer carousel 110 can be rotated or translated to align syringe 115 with reagent station 150 and/or buffer station 155. In some embodiments, reagent station 150 and/or buffer station 155 can be rotated or translated to mate with holding vessel (e.g. syringe 115). Syringe 115 can be mated with reagent station 150 to form a fluid tight connection, for example, using a Luer Lock or similar device, and plunger 120 can be used to draw fluid in from a reagent station 150. Alternatively, plunger 120 can be used to expel fluid from syringe 115 into a reagent station 150 and used to draw the expelled fluid together with any reagent fluid contained within the reagent station 150 into syringe 155. Similarly, syringe 115 can be mated with buffer station 155 to form a fluid tight connection, for example using a Luer Lock or similar device, and plunger 120 can be used to draw fluid in from a buffer station 155. Alternatively, plunger 120 can be used to expel fluid from syringe 115 into a buffer station 155 and used to draw the expelled fluid together with any buffer fluid contained within the buffer station 155 into syringe 155. In some embodiments plunger 120 can be used to repeatedly take up and expel a small amount of air in order to agitate a fluid contained within syringe 115. In some embodiments translational motion of syringe 115 relative to the transfer carousel may be used to agitate a fluid contained within syringe 115. In some embodiments, rotational and/or translational movement of the transfer carousel may be used to agitate a fluid contained within syringe 115.

In some embodiments a fluid transfer system 100 may further comprise one or more heat vents 140. Such heat vent 140 may be used to control the temperature of a fluid contained within syringe 115, for example, during a culturing, incubation, or other process.

In some embodiments, a fluid transfer system 100 may further comprise one or more analysis stations 145. Transfer carousel 110 can be rotated or translated to align syringe 115 with analysis station 145. In some embodiments, analysis station 145 can be rotated or translated to mate with holding vessel (e.g. syringe 115) or another fluid vessel or component of the fluid transfer system 100. Analysis station 145 may be a spectroscopy port and may include a light source, such as a UV-Vis light source, and/or an IR light source. Analysis station 145 may further include a detector for detecting the light source. In some embodiments analysis station 145 may include capacitive and (related) impedance sensing instrumentation that can be used, for example, to infer the composition of a cell culture (approximate cell counts etc.). In some embodiments analysis station 145 may include one or more Microbial Fuel Cell sensors in the plunger cap. In some embodiments analysis station 145 may include a dye-based sensing system (e.g. litmus paper, camera-based pH sensor that uses litmus paper, a mix of immuno-capture and specific proteolysis indicators to measure bacterial activity, etc.). In some embodiments analysis station 145 may include a surface plasmon resonance detector. In some embodiments analysis station 145 may include a sensor that can estimate refractive index of an aliquot (and thereby infer something about composition of a culture) (e.g. hyperspectral synthetic schlieren imaging). In some embodiments analysis station 145 may include a differential colorimeter (e.g. using an LED). In some embodiments analysis station 145 may include instrumentation for low cost cytometry (e.g. using laser source and detectors appropriated from CD/DVD reader). In some embodiments analysis station 145 may include instrumentation for Giant Magneto Resistance sensing (e.g. using sensors appropriated from hard-drives. In some embodiments analysis station 145 may include a graphene/antibody-capture field effect transistor.

In some embodiments a fluid transfer station comprises a peripheral station, such as an analysis station that includes a fine-pitch, lensless imaging sensor and a collimated light source. In some embodiments a peripheral station, such as an analysis station can include a fine-pitch imaging sensor and a broadband light source. Optionally, a peripheral station can further a diffraction grating. A fine-pitch, lensless imaging sensor and a collimated light source can be used, in some embodiments, to estimate cell viabilities and cell densities in a culture fluid that is sampled from a holding vessel (e.g. syringe) of the fluid transfer system. In some embodiments a fine-pitch, lensless imaging sensor can be used to perform spectral analysis of a culture fluid that is sampled from a holding vessel (e.g. syringe) of the fluid transfer system. A fine-pitch imaging sensor and a broadband light source and a diffraction grating can be used, in some embodiments, to perform hyper-spectral analysis of a culture fluid that is sampled from a holding vessel (e.g. syringe) of the fluid transfer system. In some embodiments a peripheral station can use imaging in concert with common, multivariate analytical techniques, such as Partial Least Squares Regression, Gaussian Process Regression, Support Vector Machines etc. in order to estimate process parameters such as cell viability, cell density, titer of target compounds etc. For example, fluorescence imaging can be used to estimate process parameters such as cell viability, cell density, titer of target compounds, etc. for organisms that express fluorescent markers.

In some embodiments, a fluid transfer system according to the invention is arranged so that a transfer carousel may pass a culture vessel over a shared, non-contact analytical sensor that is able to obtain useful analytical information about the culture. In some embodiments the non-contact analytical sensor may be an optical sensor, an imaging sensor, a capacitive sensor, or other type of sensor. In some embodiments the fluid transfer system's inherent tracking capabilities are able to relate the able to relate the analytical results to a particular culture vessel. In some embodiments the particular culture vessel contains an organism that was inoculated with a particular DNA sequence.

In some embodiments, transfer carousel 110 may be rotated and/or translated to position syringe 115 in the path of a light source of analysis station 145, so that the contents of syringe 115 may be monitored and/or analyzed. In other embodiments an analysis station 145 may comprise an analysis vessel capable of holding a fluid and having an opening, which can be mated to syringe 115 to allow for exchange of fluid between the analysis vessel and syringe 115. The mating may form a fluid tight connection such that fluid exchanged between the analysis vessel and the syringe 115 does not leak outside the connection. For example, such a fluid tight connection may be accomplished through the use of a Luer Lock or similar device. In some embodiments the analysis vessel may be removed from the fluid transfer system 100 (e.g., may be accessible from outside the "closed box" embodiment of a fluid transfer system) and the fluid contained therein may be analyzed using any tools available to the user.

In some embodiments, a fluid transfer system further comprises a fluid loading station 160. Fluid loading station 160 may engage directly with a holding vessel (e.g. syringe) 115. In other embodiments, a fluid loading station may optionally comprise a loading vessel capable of holding a fluid and having an opening which can be mated to syringe 115 to allow for exchange of fluid between the loading vessel 162 and syringe 115. The mating may form a fluid tight connection such that fluid exchanged between the loading vessel 162 and the syringe 115 does not leak outside the connection. For example, such a fluid tight connection may be accomplished through a disposable liquid-exchange interface/membrane 163 that uses Luer Locks or similar devices to lock the vessel 162 to the syringe 115. In some embodiments the loading vessel 162 may be a syringe having a tubular body, an opening at one end and a plunger positioned within the body.

In some embodiments, the fluid loading station 160 can be rotated and/or translated so that the loading vessel can be moved to various positions. For example, fluid loading station 160 may be rotated and/or translated so that the loading vessel 162 may be mated with syringe 115, fluid supply rig 165, chromatography rig 170, vortex 175, waste collection station 180, or other peripheral module or apparatus. When the loading vessel 162 is mated with syringe 115, or other vessel capable of containing a fluid (e.g., fluid supply rig 165, a chromatography rig 170, a centrifuge 175, and/or a waste collection station 180, or other peripheral module), a connection is formed such that fluid can be exchanged between the loading vessel 162 and the syringe 115 (or other vessel). The connection between syringe 115 and loading vessel 162 can be fluid tight so that while fluid can be exchanged between the loading vessel 162 and the syringe 115 (or other vessel), the fluid does not leak to outside of the connection (e.g. using a Luer Lock or similar device). A driver and motor can be used to control the speed at which the loading station is rotated and/or translated and the position into which the fluid loading station 160 is moved.

In some embodiments, a fluid transfer system 100 further comprises a fluid supply rig 165. In some embodiments, fluid supply rig 165 comprises at least one supply vessel capable of holding a fluid, wherein the supply vessel 167 has an opening that can be mated with holding vessel (e.g. syringe) 115. In other embodiments the supply vessel 167 is capable of being mated with a loading vessel 162 to allow fluid transfer between the supply vessel 167 and the loading vessel 162. The mating between supply vessel 167 and holding vessel 115, supply vessel 167 and loading vessel 162, or supply vessel 167 and any other vessel intended for fluid transfer, may form a fluid tight connection such that fluid exchanged between the supply vessel 167 and the holding vessel 115, loading vessel 162, or other vessel does not leak outside the connection. For example, such a fluid tight connection may be accomplished through the use of a Luer Lock or similar device. In some embodiments fluid supply rig 165 includes a plurality of supply vessels 167, which may be moved to provide an additional or different fluid to the holding vessel 115, loading vessel 162, or other vessel. Such movement may be accomplished via a conveyor belt or other automated system. In some embodiments, fluid supply rig 165 may further include a cooling unit. In some embodiments reagent station 150 and/or buffer station 155 may be refilled with fluid from a supply vessel 167 through use of the loading vessel 162 and syringe 115. Loading vessel 162 can be used to draw fluid from a supply vessel 167, and the fluid loading station 160 and/or the transfer carousel 110 can be rotated and/or translated to position mate vessel and syringe 115 to form a connection through which fluid can be exchanged. Plungers can be used to eject fluid from the loading vessel and withdraw fluid into syringe 115. The transfer carousel 110 can then be rotated and/or translated to mate syringe 115 with reagent station 150 or buffer station 155 to form a connection through which fluid can be exchanged. Plunger 120 can be used to eject fluid from syringe 115 into reagent station 150 or buffer station 155. It should be noted that other stations can be added to the system. In some embodiments, the stations may be modular and/or replaceable. Alternatively one or more stations can be emptied and/or filled using the system of the present invention and a supply rig 165. In some embodiments the input/out supply rig 165 will utilize an automated conveyor belt system that can align specific vessels with the fluid loading station 160. This rig can be programmatically controlled (i.e., scripted via software routines) such that the loading vessel 162 can load/onload fluids to the transfer carousel 110 in specific amounts and/or in specific orders. This setup will allow users to supply DNA, reagents, buffer solutions in an automated fashion as well as unload the individual outcomes of the experiments from the rig for further processing. Such automation will allow users 1) to design individual experiments with unique set of parameters for every syringe 2) Or run multi-syringe experiments which can combinatorially mix different parts to test multiple hypotheses.

In some embodiments a peripheral station may include contain one or more reservoirs (e.g. a dispensing reservoir) that can be moved into place individually to accept communication of fluids from the individual holding vessels (e.g. syringes) of the fluid transfer system for the sake of preventing exchange between individual culture vessels within the culture system. In some embodiments the peripheral station can be configured so that said exchange takes place between short, disposable couplings that are used for only one exchange. In some embodiments a dispensing reservoir is a disposable item. In some embodiments the disposable reservoirs can be withdrawn from a cassette that can hold multiple disposable reservoirs.

In some embodiments the fluid transfer system 100 can be built as a reconfigurable "rack" where additional components such as glassware, tubing, tools or equipment can be added to meet application-specific needs. For instance, the fluid transfer system 100 can be customized for DNA assembly by incorporating a different fluid supply rig 165 and by utilizing the transfer carousel 110 for combinatorial nucleotide synthesis. In another embodiment, fluid transfer system 100 can be customized for mammalian cell culturing by incorporating additional hardware (e.g. to supply $CO_2$, and/or monitor pH and/or humidity). A "rack" may also include multiple copies of the same part. For instance users can customize their rack by adding two fluid supply rigs 165 instead of having a centrifuge 175.

In some embodiments a fluid transfer system 100 can also be extended by stacking multiple fluid transfer system racks onto each other, allowing the creation of multi-rack platforms that can be networked with each other. Such embodiments may run multiple experiments through supervisory closed-loop control systems that can monitor the parameters and data analytics of multiple transfection, incubation, and lysis processes that can be carried in parallel at different racks.

In some embodiments a fluid transfer system 100 includes a peripheral module that is capable of assembling DNA sequences from modular parts according to an encoded plan. In some embodiments the same peripheral station can be used to subsequently transfect target organisms with the assembled DNA sequences to create a novel organism. In some embodiments the encoded plan is conveyed dynamically to the peripheral module via a computer network. In some embodiments the encoded plan is a computer executable program.

In some embodiments a fluid transfer system 100 further includes a chromatography rig 170, a vortex or centrifuge 175, and/or a waste collection station 180. Other peripheral modules and/or peripheral stations that would be useful in fluid processing and/or analysis may be included in a fluid transfer system according to the invention, wherein other such peripheral modules and/or stations utilize the same fluid transfer principles described herein. For example, fluid loading station 160 can be used to transfer fluid from syringe 115 to chromatography rig 170, vortex or centrifuge 175, a waste collection station 180, or other peripheral module. In some embodiments a peripheral station may include multiple reservoirs that can be moved into place individually to accept communication of fluids from the individual syringes 115 for the sake of preventing exchange between individual syringes 115 within the fluid transfer system. In some embodiments a peripheral station may include multiple reservoirs that can be moved into place individually to accept communication of fluids from the individual syringe 115 of the fluid transfer system for the sake of preventing exchange between individual syringes 115 within the fluid transfer system, and wherein said exchange takes place between short, disposable couplings that are used for only one exchange. In some embodiments, transfer carousel 110 can be rotated or translated to align syringe 115 with chromatography rig 170, a vortex or centrifuge 175, a waste collection station 180, and/or other peripheral module. In some embodiments, chromatography rig 170, a vortex or centrifuge 175, a waste collection station 180, and/or other peripheral module can be rotated or translated to mate with holding vessel (e.g. syringe 115) or another fluid vessel or component of the fluid transfer system 100.

In some embodiments, the fluid transfer system includes one or more computers having one or more processors and memory (e.g., one or more nonvolatile storage devices). In some embodiments, memory or computer readable storage medium of memory stores programs, modules and data structures, or a subset thereof for a processor to control and run the various systems and methods disclosed herein. In some embodiments, a non-transitory computer readable storage medium having stored thereon computer-executable instructions which, when executed by a processor, perform one or more of the methods disclosed herein.

The present invention also includes methods of transferring a fluid. In some embodiments a method of transferring fluid includes loading a fluid in a peripheral module; mating a syringe with the peripheral module to form a connection through which fluid can be exchanged, wherein the syringe is connected to a transfer carousel; drawing the fluid from the peripheral module into the syringe; rotating or translating the transfer carousel and optionally translating the syringe relative to the transfer carousel to align the syringe with a loading station; mating the syringe with the loading station to form a connection through which fluid can be exchanged; and ejecting fluid from the syringe into the loading station. In some embodiments the transfer carousel can be rotated and/or translated as described herein; in some embodiments the loading station may be rotated and/or translated as described herein.

Methods of transferring a fluid of the present invention can be useful for transferring cell material. In some embodiments the fluid may to be transferred may be a cell material.

In some embodiments, methods of transferring a fluid include transfecting a cell material. In such embodiments the peripheral module may be a transfection station, such as an electroporation station. Accordingly, some embodiments of the invention include adding genetic material to a cell material in a transfection station under conditions sufficient to transfect the cell material; transfecting the cell material to form transfected cell material; and allowing the transfected cell material to incubate in the syringe. In some embodiments the transfecting step may be electroporation or other transfection method known to a person of skill in the art.

In some embodiments, methods of transferring a fluid include rotating or translating the loading station to align the loading station with a second peripheral module; mating the loading station with the second peripheral module to form a connection through which fluid can be exchanged; and ejecting fluid from the loading station into the second peripheral module.

As described herein, a second peripheral module may be any additional supply or device useful for processing and/or analyzing a fluid. In some embodiments, the second peripheral module may be a fluid supply rig, a waste receptacle, a chromatography rig, a centrifuge, etc.

In some embodiments, the peripheral module may include a vessel for containing liquid, wherein the vessel is labeled with a bar code, a QR code, a fiducial marker, or a NFC tag. In such embodiments, the method may further include tracking the progress of the fluid through the fluid transfer system using the bar code, QR code, a fiducial marker, or NFC tag.

It will be appreciated by those skilled in the art that changes could be made to the exemplary embodiments shown and described above without departing from the broad inventive concepts thereof. It is understood, therefore, that this invention is not limited to the exemplary embodiments shown and described, but it is intended to cover modifications within the spirit and scope of the present invention as defined by the claims. For example, specific features of the exemplary embodiments may or may not be part of the claimed invention and various features of the disclosed embodiments may be combined.

Unless specifically set forth herein, the terms "a", "an" and "the" are not limited to one element but instead should be read as meaning "at least one".

It is to be understood that at least some of the figures and descriptions of the invention have been simplified to focus on elements that are relevant for a clear understanding of the invention, while eliminating, for purposes of clarity, other elements that those of ordinary skill in the art will appreciate may also comprise a portion of the invention. However, because such elements are well known in the art, and because they do not necessarily facilitate a better understanding of the invention, a description of such elements is not provided herein.

Further, to the extent that the methods of the present invention do not rely on the particular order of steps set forth herein, the particular order of the steps should not be construed as limitation on the claims. Any claims directed to the methods of the present invention should not be limited to the performance of their steps in the order written, and one skilled in the art can readily appreciate that the steps may be varied and still remain within the spirit and scope of the present invention.

Embodiments of the present invention may improve the economics, efficiency and safety of the current state of the art by making a closed, miniaturized process that can handle most stages of the cell culture process automatically. By miniaturizing the process, using innovative liquid transfer and processing mechanisms, and standardizing the invariant parts of the process (e.g. the concept of material transfer), the process may become highly modular, customizable, and comparatively inexpensive.

Some embodiments of the present invention may provide the following benefits: Some embodiments of fluid transfer systems according to the invention provide an all-in-one platform that supports every stage of microbial design: electroporation, incubation, purification, and lysis for running design and research experiments involving genetically modified organisms. Some embodiments may reduce labor by virtue of high degree of automation. Some embodiments may minimize or eliminate loss of containment risks, due to closed and automated nature of system. Some embodiments may minimize or eliminate external contamination risks, due to the closed and automated nature of system. Some embodiments may minimize or eliminate risks of sample mishandling or mislabeling etc., since cell cultures may be automatically ushered through the process, and each cell culture may be kept distinct from others in the system and tracked automatically at every step. Because samples may be continuously monitored and analyzed in some embodiments, some embodiments of the invention offer finer control over process parameters (e.g. temperature, gas tension, nutrient levels etc.) than is normally obtainable in a typical lab setting. Some embodiments allow high-throughput and isolated design experiments. Multiple target DNA designs can be inserted independently into microorganisms in an automated way to test multiple design options. Some embodiments of the invention use standardized off-the-shelf consumables (i.e., syringes) that can easily be replaced by the users. In some embodiments a fluid transfer system can be customized for different applications and also used for testing existing protocols offered by third party biotech companies. Some embodiments may give superior data history and analytics, since each cell culture may be monitored continuously for the sake of process control. These process control values can be historized and such historical records may be easily retrieved if there is value to be obtained from the historical data. Some embodiments may reduce the overall equipment requirements and disposable lab waste by eliminating unnecessary transfer and offline analysis operations. This feature may be especially useful for designers and researchers who do not have specialized lab environments to run their experiments. Some embodiments of the invention may improve utilization of expensive pieces of cell culture equipment, such as electroporators. For example, if one could use an electroporator nearly continuously and in an automated fashion, it would be possible to electroporate millions of samples per year, which would represent a utilization improvement of such a device by at least three orders of magnitude.

By virtue of the combined effect of the above named benefits, and by virtue of the fact that that these benefits, in combination, largely remove systemic cost and space constraints, embodiments of the fluid transfer system may allow overall higher throughput for cell culture while reducing expenses. A suitably crafted product based on the present invention may improve cell culture cost effectiveness in certain cases by several orders of magnitude.

In some embodiments, the present invention involves a suite of devices and methods that, together, comprise a design and biosynthesis platform for high-throughput, automated cell culture. Based on its unique characteristics, in some embodiments the system is particularly well suited to integrate into general research and bioinformatics as they relate to cell culture. In some embodiments, the system may also be inexpensive in relation to the prior art, and as such it may be used for nontraditional applications, such as the use of cell culture in product design, art or the small scale production of special compounds via cell culture.

Some embodiments of the invention advantageously use specialized, low-cost, cell culture containers that can be used for multiple phases of the cell culture process. This, in turn, may permit a radical reduction in transfer equipment (i.e., pipettes, pumps, "piping", glassware etc.). The combination of these factors may permit the footprint of the cell culture hardware to be extremely small. Furthermore, by making extensive use of miniaturized process control hardware, the some embodiments of the fluid transfer system (also referred to herein as the "platform") minimizes or eliminates the need for human intervention with a culture in nearly all phases of its process life-cycle.

Embodiments having a small footprint and high level of automation can result in a system that can be kept essentially closed over most important phases of the culture process. Indeed, the embodiments of the fluid transfer system lend themselves to an approach where raw "ingredients" for cell culture (cells, plasmids, special reagents etc.) could be inserted, irreversibly, into the platform. The closed nature of embodiments of the platform greatly reduces the risk of external contamination and it also lends embodiments of the platform to use in situations where loss of containment would be highly undesirable (e.g. when working with novel genetic modifications or organisms that pose pathogenic risks). Hence, the raw cell culture materials may enter in an essentially benign state (e.g. "plasmids, bacteria, nutrients and consumables") and, with suitable post-processing within the platform, emerge in an equally benign state (e.g. "vials containing lysate and miscellaneous containers of sterilized consumables").

Some advantages of embodiments of the present invention include 1) keeping the transfer of liquids to an absolute minimum; adopting a "total automation" strategy; and taking a systems-oriented view to pursue the "minimal transfer" and "total automation" objectives while also identifying and fostering opportunities for secondary benefits (i.e., modularity, customization) that arise in the course of designing various embodiments.

While many aspects of this "systems oriented" approach are evident in the following description of an exemplary embodiment of the present invention, it is worth briefly citing a few items here, for the sake of illustration. First, consider that the exemplary embodiment features a "culture vessel", which is the primary containment vessel for most of the operations involved in a cell culture batch; in a traditional approach, a different vessel would typically be used for each distinct operation, and one or more transfers of the culture would be undertaken as a result. Next, consider that embodiments of the present invention replace some of the traditional biology and wet-chemistry methods typically used in normal cell culture practice with in-line, process analytical methods. Finally, the present invention contemplates reformulation of some of the reagents that are typically used in a multi-vessel approach—for example, the exemplary implementation describes a situation where the culture vessel ends up with traces of electroporation buffer, some recovery medium, some antibiotics and finally a conventional nutrient medium. Since these various media are seldom intermingled, it is contemplated that a user could make minor adjustments to formulations so that the medium has suitable composition at each step. All of these design elements come together to contribute to the high degree of automation embodied in some embodiments fluid transfer systems of the invention, and their overall compactness.

Definitions

Analytics (or process analytics)—a body of techniques that usually use modeling of some sort (first principles modeling, statistical modeling etc.) to indirectly measure parameters of interest in a process. For example, differential dynamic microscopy (DDM) can be used to estimate cell culture density and viability using inexpensive optical sensors.

DNA—deoxyribonucleic acid, a self-replicating material present in nearly all living organisms as the main constituent of chromosomes. It is the carrier of genetic information.

Electrocompetent cells—concentrated cell populations that have been treated and held in conditions that typically minimize the concentration of ions in the cell and in the suspension medium. Cells are typically made electrocompetent via repeated cycles of washing and centrifugation at reduced temperatures in special media.

Electroporation—a technique that is used to disrupt a cell membrane by exposing the cell to a brief, intense electric field. In the context of cell culture, the technique is used as an efficient means of introducing foreign DNA into an organism.

Electroporation cuvette—A specialized cuvette that holds a small amount of liquid (on order of 100s of nano-liters) of liquid that contains plasmids and electrocompetent organisms for the purposes of introducing said plasmids into said organisms by means of electroporation.

GMO—A GMO is an organism whose genetic material has been altered by the techniques of genetic engineering so that it contains one or more genes not normally found there.

Lysate—the material resulting from the lysis (intentional disintegration) of cells Lysis—the process of intentionally disintegrating cells, using any combination of mechanical, chemical etc. methods, for the purpose of extracting materials from them.

Plasmid—a genetic structure in a cell that can replicate independently of the chromosomes, typically a small circular DNA strand in the cytoplasm of a microorganism, bacterium or protozoan.

Smart Plug—a structure within the body of a syringe-like vessel that contains any combination of electronic, optical, mechanical or chemical mechanisms that perform a useful function with regard to culturing cells with the syringe-like vessel. In most cases, a smart plug will occupy a reserved portion of the syringe body near the tip of the syringe, and will permit fluid to pass through a bore that extends the bore of the syringe tip. Accordingly, the smart plug adds capabilities without detracting from the basic function of the syringe, apart from slightly reducing its overall volume.

Station—in the context of the present invention, a station is a device that encapsulates some operation that is part of the cell culture process.

Transfection—the process of deliberately introducing nucleic acids into cells, usually for the sake of imparting some special, heritable characteristic.

EXAMPLES

While many aspects of this "systems oriented" approach are evident in the following description of an exemplary embodiment based on design plans for a prototype of the present invention, it is worth briefly citing a few items here, just for the sake of illustration. First, consider that the exemplary embodiment features a holding vessel or "culture vessel" (e.g. syringe), which is the primary containment vessel for most of the operations involved in a cell culture batch; in a traditional approach, a different vessel would typically be used for each distinct operation, and one or more transfers of the culture would be undertaken as a result. Some embodiments of the present invention replace some of the traditional biology and wet-chemistry methods typically used in normal cell culture practice with in-line, process analytical methods. It is contemplated that in some embodiments, some of the reagents that are typically used in a multi-vessel approach—for example, the exemplary implementation describes a situation where the culture vessel ends up with traces of electroporation buffer, some recovery medium, some antibiotics and finally a conventional nutrient medium, may be reformulated. Since these various media are seldom intermingled, it may be beneficial to make minor adjustments to formulations so that the medium has suitable composition at each step. So in this brief paragraph we have touched on elements of process design that span mechanical, chemical and analytical aspects of the system. All of these design elements come together to contribute to the high degree of automation embodied in the system, and its overall compactness.

Example 1: Canonical Case: Typical Transfection, Culture, Purification and Harvest of Bacterial GMO In this embodiment, the present invention is shown as a closed unit.

Material is introduced into the closed unit by inserting a special electroporation cuvette into the electroporation station. Note that the electroporation station has special features that allow an ensemble of electroporation cuvettes to be introduced at a time. These cuvettes each contain a liquid buffer that contains electrocompetent organisms and plasmids that we wish to insert into the organisms for the sake of transforming them.

Each cuvette in the electroporation station is moved into position between a pair of electrodes that make contact with corresponding electrodes on the cuvette. An electroporation device (not shown) imparts a brief, high-voltage pulse to the contents of the cuvette. This electroporation pulse briefly disrupt the cell membranes of the organisms and some of the plasmids will enter some of the host cells. It is worth noting that the details of the electroporation process vary, based on the organism being transfected and various other details. Therefore, the electroporation parameters are part of the programming of the system. The electroporation station is able to identify the particular cuvette being treated (e.g. via a bar-code on the cuvette) and select appropriate parameters for the electroporation pulse.

A designated culture vessel is moved into position adjacent to the electroporation station by the culture platform. Note that the relationship between an electroporation cuvette and a particular culture vessel is part of the programming for a given culture batch. The culture vessel is then moved towards a target area on the cuvette that contains the newly electroporated cells in such a way that it engages with the electroporation cuvette and forms a liquid transfer channel between the cuvette and itself. The culture vessel then uses an integrated plunger to withdraw the electroporated cells from the electroporation cuvette, thereby moving the electroporated cells into the culture vessel. After this, the culture vessel is moved back to its resting position on the culture platform, while the electroporation station moves the used cuvette to a discard/sterilize pile as the next electroporation cuvette moves into position. As a practical matter, the initial embodiment of the electroporation station in the present invention is anticipated to have a means of sterilizing and ejecting used cuvettes, and the electroporation station is also anticipated to have integral cooling in order to keep queued electroporation cuvettes at a designated (low) temperature as they await electroporation. Neither of these features is shown in FIG. 1.

Once the culture vessel is charged with electroporated organisms, it is moved by the culture platform until it is adjacent to the Resting Medium station. The culture platform moves the culture vessel into position such that it engages with the Resting Medium station and forms a liquid communication channel between the culture vessel and a disposable sac of Resting Medium that is held within the Resting Medium station, The culture vessel then uses its integrated plunger to withdraw a predetermined amount of resting medium from the sac.

Note that this cycle of "electroporate, load culture vessel, charge culture vessel with resting medium" cycle would typically cycle until we had loaded several (or possibly all) culture vessels on the culture platform. The details of this would vary from run to run and would be part of the batch programming for the system. Once all of the culture vessels have been charged, they typically are left to rest for a specified amount of time as the electroporated organisms recover.

Once the culture of electroporated organisms have been given a bit of time to recover, they would typically be subjected to a selection operation. This is accomplished by having the culture platform move each culture vessel, in turn, to the Selection Station (1090). The culture platform moves a given culture vessel into position such that it engages with the Selection Station and forms a liquid communication channel between the culture vessel and a disposable sac of medium that contains a particular antibiotic or some other sort of selection agent that is intended to kill off any organisms that happen to be alive in the culture, but which lack the plasmids of interest. It is worth noting the Selection Station is similar in many respects to the Recovery Station. However, the Selection Station would generally need to "know" the relationship between a given culture vessel and the appropriate antibiotic (or other selection agent) that should be dispensed, since each culture vessel may each have its own sort of organism with its own sort of plasmid, and hence just each use its own selection agent. It is also worth noting that the requirements of the Selection Station are a superset of the requirements for the Resting Medium Station, so a Selection Station could generally fulfill the Resting Medium Station and Selection Station roles. However, in this description they are shown as distinct stations for the sake of simplicity and clarity.

The vessels are given some time so that the selection agent can cull untransformed organisms from the culture. During this time, the culture vessels may use their internal plunger to draw in a little air and apply mechanical motion to the culture in order to maintain a suitable gas tension in the culture solution. The appropriate gas volume, agitation protocol, culture temperature etc. is apt to vary from culture vessel, so each segment of the cell culture platform can be outfitted with individual temperature control and agitation features.

Once the selection agent has culled the cell culture, it would typically be time to feed the cells a bolus of nutrient medium. In this exemplary embodiment, the feeding operation is accomplished by having the culture platform move each culture vessel, in turn, to the Feeding Station. The culture platform moves a given culture vessel into position such that it engages with the Feeding Station and forms a liquid communication channel between the culture vessel and a disposable sac of medium that contains a particular nutrient mix for the culture. It is worth noting the Feeding Station is similar in nearly all respects to the Selection Station, including the fact that the Feeding Station would generally need to "know" the relationship between a given culture vessel and the appropriate nutrient medium that should be dispensed, since each culture vessel may each have its own sort of organism with its own sort of plasmid, and hence may have a different nutritional profile. In some practical embodiments, there may be multi-purpose stations (e.g. Resting Station/Selection Station/Feeding Station/Reagent Station/Buffer Station) that do similar things, and vary their role simply by virtue of the reagents that they dispense for a given operation. However, in this description, the Feeding Station is shown as a separate station for the sake of simplicity and clarity.

While the cells are growing in the culture medium, it may be necessary to actively monitor their population density and viability. This can be accomplished by a number of means. One possible approach is to have a special Counter Station. In this exemplary embodiment, the feeding operation is accomplished by having the culture platform move each culture vessel, in turn, to the Counter Station. This exemplary counter station contains an array of small cuvettes, one for each culture vessel. These cuvettes each have a special fitting. In order to perform a count and viability test, the culture platform moves a given culture vessel into position such that it engages with the Counter Station and forms a liquid communication channel between the culture vessel and a designated cuvette. The culture vessel discharges an aliquot of culture fluid of a specified volume into the cuvette, where it is analyzed using special imaging techniques. It is worth noting that one can estimate cell density in the culture and viability using relatively simple techniques, such as Dynamic Differential Microscopy. Furthermore, such techniques can use inexpensive optical sensors. Indeed, inexpensive CMOS sensors, such as those used in consumer devices, are particularly well suited to the task because their small sensor pitch (often just over 1 µm) is a close match for the size of the smallest likely specimens for culture. The Counter Station is depicted with various collimated light sources, a small CMOS camera and a mechanism to rotate selected counter cuvettes into position. It is presumed that the counter station may need to clean the counter cuvettes between uses, or they may be disposable items (e.g. based on capillary tubes). Note that in some embodiments the Counter Station may be an Analysis station and may perform additional analytic functions, such as applying various "wet chemistry" analytics to the sample, such as applying spectroscopic measurements to the sample, applying fluorescence measurements to the sample etc.

In order to control the gas tension in the culture, it may be necessary to perform some gas-exchange operations. This could be achieved using a Gas Exchange Station. Based on culture protocol or analytical results, a cell culture tube could be moved to the Gas Exchange Station. The Gas Exchange station could have elaborate gas mixes available, but it is more likely that any cultures requiring gas exchange will be aerobic, in which case gas exchange involves exchanging gas in the culture vessel with ambient air that has been micro-filtered. This might assume a number of forms. In one embodiment, the gas exchange mechanism uses a series of selectable containers that are tapered at the bottom (similar to a Safe-Lock tube), one for each culture vessel. Each of these containers are fitted with a tube that communicates with the bottom of the vessel and which is terminated with a special fitting that permits access by the culture vessel. The top of the container communicates with open air by way of a microfilter that permits gases to exchange relatively freely, but which has a pore structure that is too fine to pass any cells. This exemplary gas exchange operation begins when the culture platform moves a selected culture vessel to the Gas Exchange Station. The culture platform moves a given culture vessel into position such that it engages with the Gas Exchange station and forms a liquid communication channel between the culture vessel and the access tube. The culture vessel discharges a determined amount of its contents into the gas exchange vessel, thereby pushing all gas and liquid contents into the gas exchange vessel. By virtue of gravity, any liquid culture content stays at the bottom of the gas exchange tube and any gases that were in the culture tube are permitted to pass through the micro-filters at the top. The culture tube then draws a determined volume back in, which will return all liquid culture contents to the culture vessel. If the amount drawn in exceeds the volume of the culture liquid, then that volume will be filled by gas that is drawn in through the microporous vent at the top of the gas exchange tube. Note that this "discharge/recharge" could proceed several times if it is necessary to ensure complete gas turnover. It is also worth noting that the gas exchange station could be made more elaborate, e.g. sending discharged gases to instruments such as gas chromatographs etc. for analysis, but such options are not shown.

When the culture is complete, it is commonly centrifuged in order to separate culture solids (which consist almost exclusively of cellular matter) from the purely liquid fraction of the culture (which is typically a complex mix of nutrients and cellular metabolites). In our exemplary embodiment, solids separation can be achieved by moving the contents of the culture vessel into a harvesting module, which has an integrated centrifuge, along with liquid handling capabilities. This station performs a centrifugation step to crudely separate the culture into a plug of cellular solids and a relatively solids-free supernatant. The supernatant is then decanted from the solids. In most cases, target compounds of interest are in the cellular solids, in which case the supernatant is discarded and subsequently sterilized. In other cases, the supernatant may hold the targets of interest, in which case the solids are discarded and subsequently sterilized.

In a common scenario, both the cellular solids and the supernatant may be treated with various lysates. These may be used to:
  Degrade the cell wall and cellular membranes of cultured organisms to release target proteins.
  Degrade DNA and RNA molecules that could encode pathogenic expressions.
  Transform large macromolecules (e.g. large proteins) into smaller molecules that may be the compounds of interest (e.g. target peptides).

In the exemplary embodiment, this lysation step is shown occurring within the harvesting station. Furthermore, it is common for the material to be subjected to an additional centrifugation step at this point. In fact, it is possible that the materials may go through several such chemical treatment, centrifugation and decantation steps. Since the harvest module has integrated centrifugation and liquid handling capabilities, it is able to handle arbitrarily complex cycles of centrifugation, chemical treatment and decantation. It is worth noting that cell harvest can include other mechanisms, such as sonication, as part of the protocol. In principle, it is feasible to include such features in an integrated module but we do not show this in the present embodiment.

Once the harvest unit is finished with its task, the pretreated cellular products, which are in sealed containers, are passed out of the unit for subsequent processing. This transfer-out operation would presumably involve treating the exterior of the containers so that they are free of potentially infectious materials. Subsequent treatment steps from the extraction of target agents are diverse and often complex. However, some separations are quite simple (e.g., the use of an inert immobile matrix and salt-water gradients to elute proteins with hydrophobic surface regions), and simple separation treatments of this sort would easily be implemented as a specialized "separation station" module that is perfectly consistent with the various other modules discussed in connection with the present invention. Indeed, this notion of "reprogramming the hardware" of the present invention via specialized modules with standardized form factors is one of the chief points of novelty.

Example 2: Use of Lyophilized Inoculant

This scenario is essentially identical to the canonical example, except that the cell cultures are inoculated using lyophilized organisms. Hence, candidate GMOs can be shipped as packets of freeze-dried material, kept cool with dried ice. The electroporation station is replaced with a station that handles the reconstitution of the lyophilized inoculant material in order to start a culture of the desired cells. This scenario would be particularly well suited for parties who wish to culture certain cell lines, but who do not wish to undertake the expense and complexity of developing cell lines "from scratch".

Example 3: Mammalian Culture

Mammalian cell cultures are typically cultured from cell lines. The development of mammalian cell lines is a complex task that is traditionally not well suited to a "desktop" platform. However, most aspects of mammalian cell culture are fairly similar to other types of cell culture. Mammalian cultures typically take longer to culture than bacterial cultures, the cells often more delicate, and the products of mammalian cell culture are often of significantly higher value than the products produced by simple organisms (e.g. bacteria, yeast etc.). Accordingly, it may be desirable to use more sophisticated cell culture mechanisms for mammalian cultures. In one embodiment, a variant of the cell culture "syringe" has an instrumented plunger, which permits continuous monitoring and control of pH, gas tension and nutrient levels.

It is worth pointing out that mammalian cultures are typically so expensive (over $100/gram of raw cellular material by some estimates) and the end products are often so valuable ($10000s/gram high titer material) that a suitable variant of the present invention could hold potential as a mechanism for small scale manufacture. In this scenario, its chief value is the fact that it minimizes the potential risks for external contamination (handling is minimized) and individual cultures are isolated from each other—hence if one culture tube is contaminated or otherwise fails, the issue is unlikely to spread to other culture tubes.

Example 4: Viral Culture in Mammalian Host Cells

The present invention may be ideal for highly parallelized production of candidate viral cultures for viral therapies (e.g. viruses that are engineered to attack cancerous cells). In this case, the culture protocols would be essentially the same as those for other mammalian cells. The present invention yields special benefits by virtue of its high degree of automation and its high degree of containment. These features combine to yield a platform that can achieve high throughput rates for culturing candidate viruses, while imparting a degree of inherent safety, due to the closed system nature of the design.

Viral cultures are apt to have highly specialized harvesting and post-processing steps, particularly if they are intended to recover materials for viral therapy.

Example 5: Culture of Cells Obtained from Human or Animal Patients

The present invention may be well suited for automated culture of patient cells, such as the culture of potential malignancies for subsequent evaluation. In this case, the system's compactness, high degree of automation, integrated ability to track culture vessels and inherent minimization of or freedom from cross-contamination risks are all potentially valuable in a clinical setting.

We claim:

1. A closed, automated fluid transfer system comprising:
   a transfer carousel capable of rotational and/or translational movement;
   at least one syringe comprising a plunger, wherein the syringe is connected to the transfer carousel such that the movement of the transfer carousel results in movement of the syringe and wherein the syringe is capable of translational movement relative to the transfer carousel;
   a drive motor connected to the syringe that is capable of controlling the position of the plunger, wherein the drive motor is partially or fully housed within the body of the syringe;
   a peripheral module comprising an automated transfection station, wherein the automated transfection station comprises at least one vessel that is capable of containing a fluid, wherein the vessel has an opening that can be mated with the syringe to allow fluid transfer between the vessel and the syringe; and
   an automated mobile platform, wherein the automated mobile platform is configured to bring together the syringe and the peripheral module to mate the opening of the transfection station vessel with the syringe.

2. The closed, automated fluid transfer system according to claim 1, further comprising at least a second peripheral module.

3. The closed, automated fluid transfer system according to claim 2, wherein the second peripheral module comprises a fluid loading station, wherein the fluid loading station comprises a loading vessel that is capable of containing a fluid, is capable of rotational and/or translational movement, and can be mated with the syringe to allow fluid transfer between the fluid loading station and the syringe.

4. The closed, automated fluid transfer system according to claim 3, further comprising a fluid supply rig, wherein the fluid supply rig comprises one or more supply vessels capable of containing a fluid, which can be mated with the fluid loading station to allow fluid transfer between the supply vessel and the fluid loading station.

5. The closed, automated fluid transfer system according to claim 4, wherein the fluid supply rig is capable of rotational or translational movement.

6. The closed, automated fluid transfer system according to claim 2, wherein the second peripheral module further comprises an analysis station.

7. The closed, automated fluid transfer system according to claim 3, wherein the second peripheral module further comprises a centrifuge comprising a centrifuge vessel capable of containing a fluid, wherein the fluid loading station is configured to be rotated or translated and/or the centrifuge is configured to be translated or rotated to mate the loading vessel with the centrifuge vessel to allow fluid transfer between the loading vessel and the centrifuge vessel.

8. The closed, automated fluid transfer system according to claim 3, further comprising a waste station, wherein the fluid loading station can be rotated or translated to mate the fluid loading station with the waste station to allow fluid transfer between the loading station and the waste station.

9. The closed, automated fluid transfer system according to claim 3, further comprising a chromatography rig, wherein the fluid loading station can be rotated or translated to mate the fluid loading station with the chromatography rig to allow fluid transfer between the loading station and the chromatography rig.

10. The closed, automated fluid transfer system according to claim 1, further comprising at least one motor wherein the motor controls the movement of the transfer carousel.

11. The closed, automated fluid transfer system according to claim 1, wherein the automated transfection station comprises an automated electroporation system.

12. The closed, automated fluid transfer system according to claim 6, wherein the analysis station comprises an imaging device from which data may be obtained and used to perform one or more analytical techniques selected from Partial Least Squares Regression, Gaussian Process Regression, and Support Vector Machines to estimate one or more process parameters selected from cell viability, cell density, and titer of target compounds.

13. The closed, automated fluid transfer system according to claim 6, wherein the analysis station comprises a fluorescence detector, which is capable of collecting data that can be used to estimate process parameters selected from cell viability, cell density, and titer of target compounds for organisms that express fluorescent markers.

14. The closed, automated fluid transfer system according to claim 1, wherein the peripheral module is further configured to assemble a DNA sequence from a plurality of modular parts according to an encoded plan.

15. The closed, automated fluid transfer system according to claim 2, wherein the mobile platform can bring together the syringe and the second peripheral module.

16. The closed, automated fluid transfer system according to claim 1, wherein the syringe further comprises miniaturized analytical instrumentation embedded in the plunger that is configured to monitor contents of the syringe.

17. The closed, automated fluid transfer system according to claim 1, wherein the syringe further comprises one or more ports that pass through the plunger and permit monitoring of gas tension in contents of the syringe and/or control of gas tension in the contents of the syringe.

* * * * *